(12) United States Patent
Buermann et al.

(10) Patent No.: US 10,858,701 B2
(45) Date of Patent: Dec. 8, 2020

(54) SCANNING APPARATUS AND METHOD USEFUL FOR DETECTION OF CHEMICAL AND BIOLOGICAL ANALYTES

(71) Applicant: Omniome, Inc., San Diego, CA (US)

(72) Inventors: Dale Buermann, San Diego, CA (US); Michael John Erickstad, San Diego, CA (US); Rebecca McGinley, San Diego, CA (US); Alex Nemiroski, San Diego, CA (US); Harry Scott Rapoport, San Diego, CA (US); Arnold Oliphant, Morgan Hill, CA (US)

(73) Assignee: Omniome, Inc., San Diego, CA (US)

( * ) Notice: Subject to any disclaimer, the term of this patent is extended or adjusted under 35 U.S.C. 154(b) by 62 days.

(21) Appl. No.: 15/998,727

(22) Filed: Aug. 15, 2018

(65) Prior Publication Data
US 2019/0055596 A1    Feb. 21, 2019

Related U.S. Application Data

(60) Provisional application No. 62/545,606, filed on Aug. 15, 2017.

(51) Int. Cl.
*G01N 21/13* (2006.01)
*C12Q 1/6874* (2018.01)
(Continued)

(52) U.S. Cl.
CPC ...... *C12Q 1/6874* (2013.01); *B01L 3/502715* (2013.01); *B01L 7/52* (2013.01);
(Continued)

(58) Field of Classification Search
USPC .......... 436/164, 807, 46; 422/400, 401, 560, 422/561, 563, 566; 435/6.1, 6.12
See application file for complete search history.

(56) References Cited

U.S. PATENT DOCUMENTS 3,572,888 A * 3/1971 Kawashima ........... G02B 21/26
                                                    359/393
3,765,745 A * 10/1973 Burboeck ............... G02B 21/26
                                                    359/393
(Continued)

FOREIGN PATENT DOCUMENTS

WO    WO-91/06678 A1    5/1991
WO    WO-00/63437 A2   10/2000
(Continued)

OTHER PUBLICATIONS

Bently,D.R. et al. (Nov. 6, 2008). "Accurate whole human genome sequencing using reversible terminator chemistry," *Nature* 456(7218):53-59.
(Continued)

*Primary Examiner* — Dean Kwak
(74) *Attorney, Agent, or Firm* — Mintz Levin Cohn Ferris Glovsky and Popeo, P.C.

(57) ABSTRACT

An apparatus can include a vessel, a reference surface, a preload, a scan actuator, and a transmitter. The reference surface can form a structural loop with a detector. The preload can be configured to urge the vessel to contact an area on the reference surface. The scan actuator can be configured to slide the vessel along the reference surface in a scan dimension. The transmitter can be configured to direct signal from the vessel to a detector and/or direct energy from an energy source to the vessel, when the vessel is urged by the preload to contact the reference surface.

29 Claims, 18 Drawing Sheets

(51) Int. Cl.
  *B01L 3/00* (2006.01)
  *B01L 7/00* (2006.01)
  *G01N 21/64* (2006.01)
  *B01L 9/00* (2006.01)
  *G01N 21/03* (2006.01)
  *G01N 21/05* (2006.01)

(52) U.S. Cl.
  CPC .......... *B01L 9/52* (2013.01); *G01N 21/03* (2013.01); *G01N 21/13* (2013.01); *G01N 21/645* (2013.01); *G01N 21/6428* (2013.01); *B01L 3/527* (2013.01); *B01L 2300/0877* (2013.01); *B01L 2300/1822* (2013.01); *B01L 2400/0487* (2013.01); *G01N 21/05* (2013.01); *G01N 2021/0346* (2013.01); *G01N 2021/0375* (2013.01); *G01N 2021/6439* (2013.01)

(56) References Cited

U.S. PATENT DOCUMENTS

| | | | |
|---|---|---|---|
| 4,012,112 A | 3/1977 | Masterson | |
| 4,704,013 A * | 11/1987 | Clark | G02B 21/241 359/383 |
| 4,902,132 A * | 2/1990 | Murphy, Jr. | G01N 15/1468 356/244 |
| 5,130,238 A | 7/1992 | Malek et al. | |
| 5,455,166 A | 10/1995 | Walker | |
| 5,587,833 A * | 12/1996 | Kamentsky | G01N 1/2813 250/201.3 |
| 5,641,658 A | 6/1997 | Adams et al. | |
| 5,695,934 A | 12/1997 | Brenner | |
| 5,863,722 A | 1/1999 | Brenner | |
| 5,888,737 A | 3/1999 | DuBridge et al. | |
| 6,140,489 A | 10/2000 | Brenner | |
| 6,151,161 A * | 11/2000 | Mayer | G02B 21/24 359/392 |
| 6,175,002 B1 | 1/2001 | DuBridge et al. | |
| 6,214,587 B1 | 4/2001 | Dattagupta et al. | |
| 6,266,459 B1 | 7/2001 | Walt et al. | |
| 6,355,431 B1 | 3/2002 | Chee et al. | |
| 6,770,441 B2 | 8/2004 | Dickinson et al. | |
| 6,859,570 B2 | 2/2005 | Walt et al. | |
| 7,057,026 B2 | 6/2006 | Barnes et al. | |
| 7,115,400 B1 | 10/2006 | Adessi et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,329,860 B2 | 2/2008 | Feng et al. | |
| 7,405,281 B2 | 7/2008 | Xu et al. | |
| 7,622,294 B2 | 11/2009 | Walt et al. | |
| 8,252,911 B2 | 8/2012 | Bjornson et al. | |
| 8,530,164 B2 | 9/2013 | Patel et al. | |
| 8,951,781 B2 | 2/2015 | Reed et al. | |
| 9,073,033 B2 | 7/2015 | Lebl et al. | |
| 9,193,996 B2 | 11/2015 | Buermann et al. | |
| 9,476,080 B2 | 10/2016 | Li et al. | |
| 9,581,550 B2 | 2/2017 | Rulison et al. | |
| 10,501,796 B2 | 12/2019 | Buermann et al. | |
| 2002/0055100 A1 | 5/2002 | Kawashima et al. | |
| 2004/0002090 A1 | 1/2004 | Mayer et al. | |
| 2004/0096853 A1 | 5/2004 | Mayer | |
| 2005/0064460 A1 | 3/2005 | Holliger et al. | |
| 2005/0130173 A1 | 6/2005 | Leamon et al. | |
| 2007/0099208 A1 | 5/2007 | Drmanac et al. | |
| 2007/0128624 A1 | 6/2007 | Gormley et al. | |
| 2008/0009420 A1 | 1/2008 | Schroth et al. | |
| 2008/0108082 A1 | 5/2008 | Rank et al. | |
| 2009/0026082 A1 | 1/2009 | Rothberg et al. | |
| 2009/0127589 A1 | 5/2009 | Rothberg et al. | |
| 2009/0197326 A1 | 8/2009 | El Gamal et al. | |
| 2009/0247414 A1 | 10/2009 | Obradovic et al. | |
| 2010/0111768 A1 * | 5/2010 | Banerjee | C12Q 1/6869 422/82.08 |
| 2010/0137143 A1 | 6/2010 | Rothberg et al. | |
| 2010/0282617 A1 | 11/2010 | Rothberg et al. | |
| 2012/0002276 A1 * | 1/2012 | Suzuki | G02B 21/26 359/391 |
| 2012/0270305 A1 | 10/2012 | Reed et al. | |
| 2015/0293021 A1 | 10/2015 | Finkelstein et al. | |
| 2016/0017416 A1 | 1/2016 | Boyanov et al. | |
| 2016/0076025 A1 | 3/2016 | Boutell et al. | |
| 2016/0356715 A1 | 12/2016 | Zhong et al. | |
| 2017/0022553 A1 | 1/2017 | Vijayan et al. | |
| 2017/0191125 A1 | 7/2017 | Vijayan et al. | |
| 2018/0044727 A1 | 2/2018 | Vijayan et al. | |
| 2018/0187245 A1 | 7/2018 | Dambacher et al. | |
| 2018/0208983 A1 | 7/2018 | Dambacher et al. | |
| 2018/0280975 A1 * | 10/2018 | Kilcoin | C12Q 1/6869 |
| 2019/0055598 A1 | 2/2019 | Buermann et al. | |
| 2020/0063201 A1 | 2/2020 | Buermann et al. | |

FOREIGN PATENT DOCUMENTS

| | | |
|---|---|---|
| WO | WO-00/63437 A3 | 10/2000 |
| WO | WO-2004/018497 A2 | 3/2004 |
| WO | WO-2004/018497 A3 | 3/2004 |
| WO | WO-2005/010145 A2 | 2/2005 |
| WO | WO-2005/010145 A3 | 2/2005 |
| WO | WO-2005/065814 A1 | 7/2005 |
| WO | WO-2007/095090 A2 | 8/2007 |
| WO | WO-2007/095090 A3 | 8/2007 |
| WO | WO-2007/123744 A2 | 11/2007 |
| WO | WO-2007/123744 A3 | 11/2007 |
| WO | WO-2012/096703 A1 | 7/2012 |
| WO | WO-2016/154193 A1 | 9/2016 |
| WO | WO-2019/035897 A1 | 2/2019 |

OTHER PUBLICATIONS

Dean, F.B. et al. (Apr. 16, 2002). "Comprehensive human genome amplification using multiple displacement amplification," *PNAS USA* 99(8):5261-5266.

Dressman, D. et al. (Jul. 22, 2003, e-published Jul. 11, 2003). "Transforming single DNA molecules into fluorescent magnetic particles for detection and enumeration of genetic variations," *PNAS USA* 100(15):8817-8822.

Korlach, J. et al. (Jan. 29, 2008, e-published Jan. 23, 2008). "Selective aluminum passivation for targeted immobilization of single DNA polymerase molecules in zero-mode waveguide nanostructures," *PNAS USA* 105(4):1176-1181.

Lage, J.M. et al. (Feb. 2003). "Whole genome analysis of genetic alterations in small DNA samples using hyperbranched strand displacement amplification and array-CGH," *Genome Res* 13(2):294-307.

Levene, M.J. et al. (Jan. 31, 2003). "Zero-mode waveguides for single-molecule analysis at high concentrations," *Science* 299(5607):682-686.

Lizardi, P.M. et al. (Jul. 1998). "Mutation detection and single-molecule counting using isothermal rolling-circle amplification," *Nat Genet* 19(3):225-232.

Lundquist, P.M. et al. (May 2008). "Parallel confocal detection of single molecules in real time," *Opt Lett* 33(9):1026-1028.

Walker, G.T. et al. (Apr. 11, 1992). "Strand displacement amplification—an isothermal, in vitro DNA amplification technique," *Nucleic Acids Res* 20(7):1691-1696.

Written Opinion dated Jul. 19, 2019, for PCT Application No. PCT/US2018/000164, filed Aug. 5, 2018, 6 pages.

Anonymous (Sep. 6, 1998). "Molecular Expressions Microscopy Primer: Anatomy of the Microscope—Microscope Stages," located at <https://micro.magnet.fsu.edu/primer/anatomy/stage.html> 6 pages.

Kern, M.A. (Sep. 3, 2005). "Stage-extension device for transmission light microscopes," *The Royal Microscopical Society Journal of Microscopy*, 219:157-159.

International Search Report dated Nov. 7, 2018 for PCT Application No. PCT/US2018/000164, filed Aug. 15, 2018, 6 pages.

(56) References Cited

OTHER PUBLICATIONS

Written Opinion dated Nov. 7, 2018 for PCT Application No. PCT/US2018/000164, filed Aug. 15, 2018, 8 pages.

\* cited by examiner

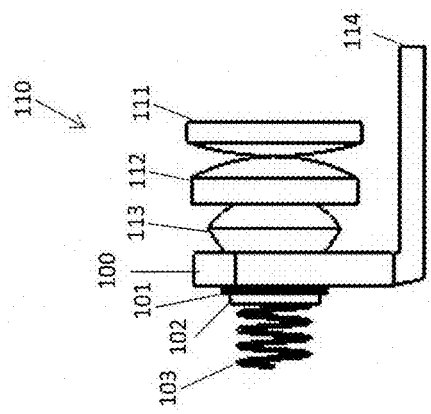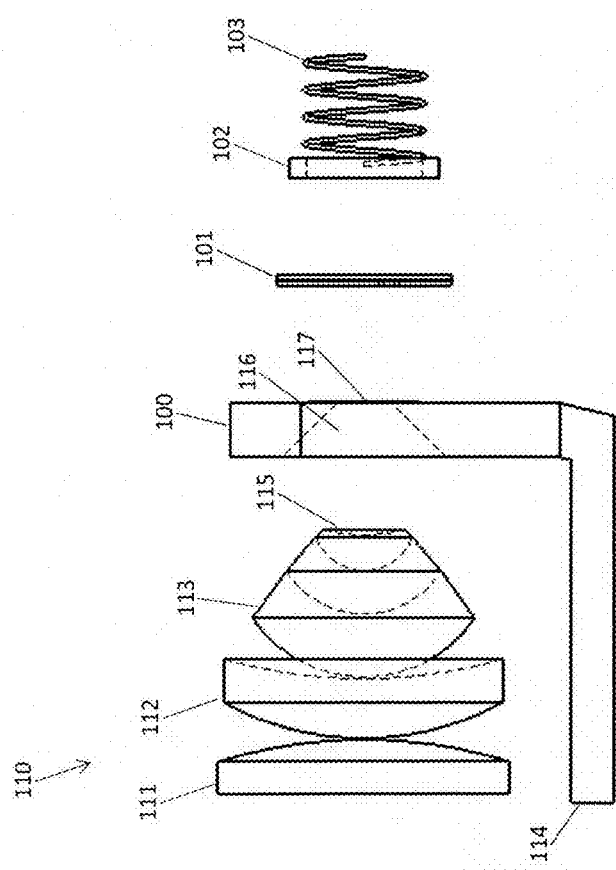

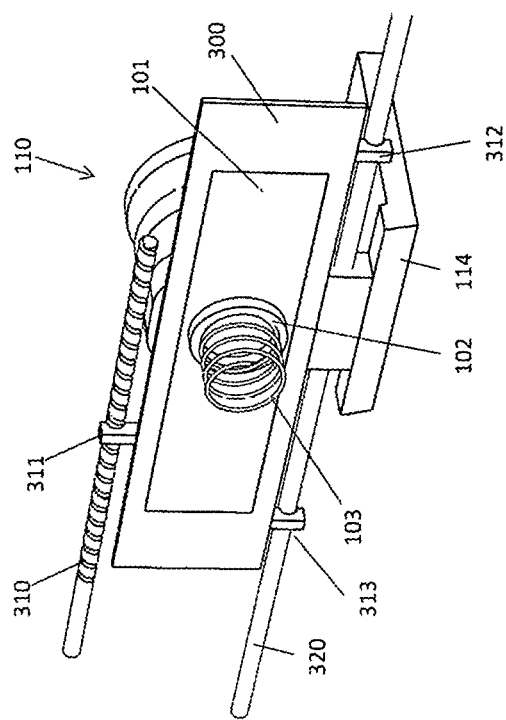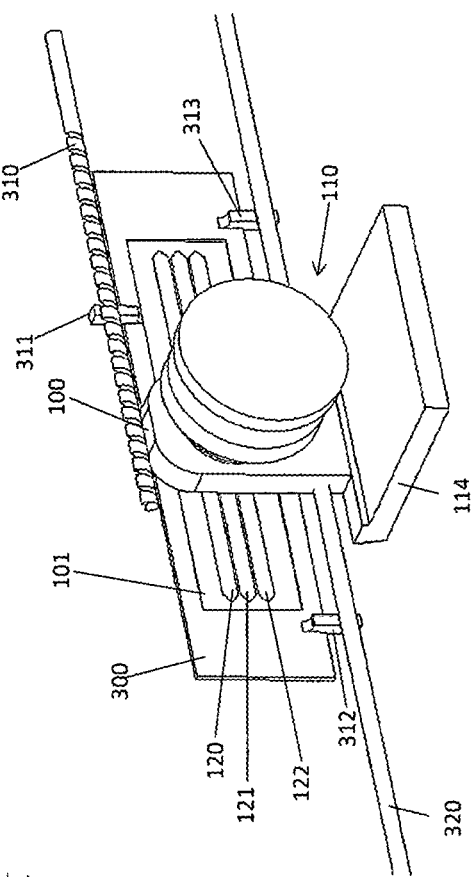
FIG. 6A
FIG. 6B

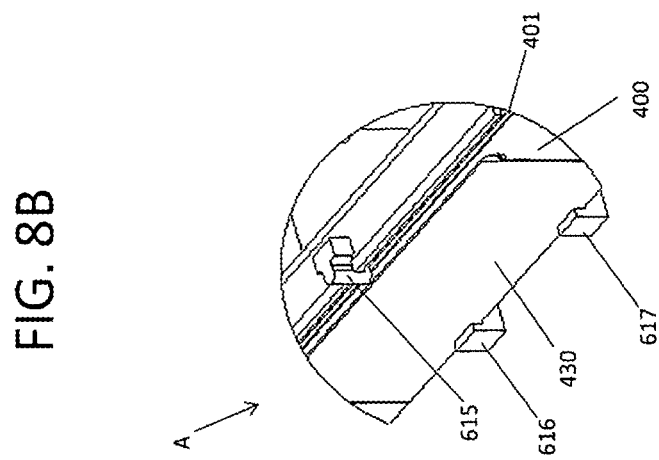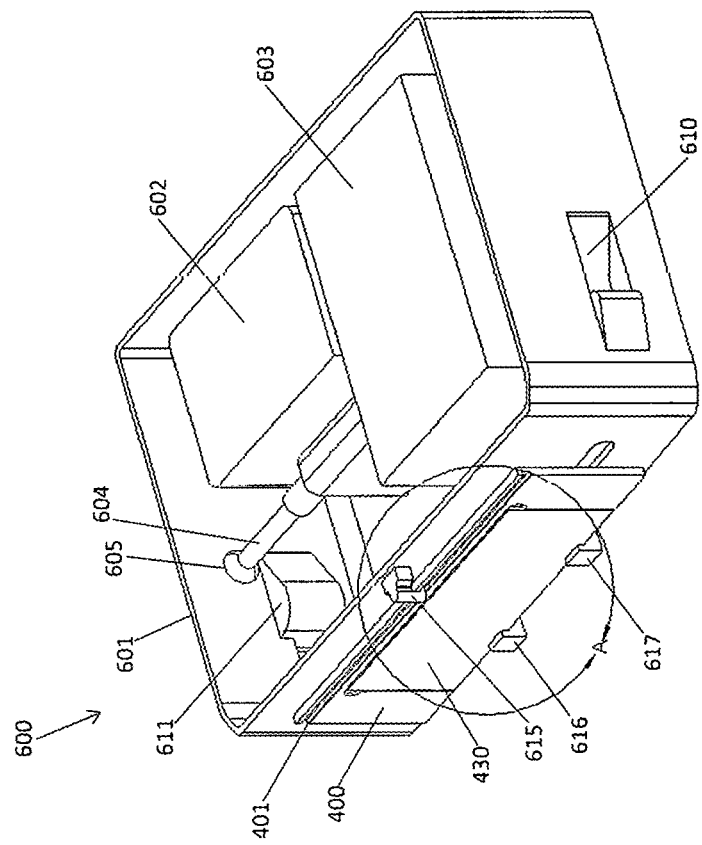

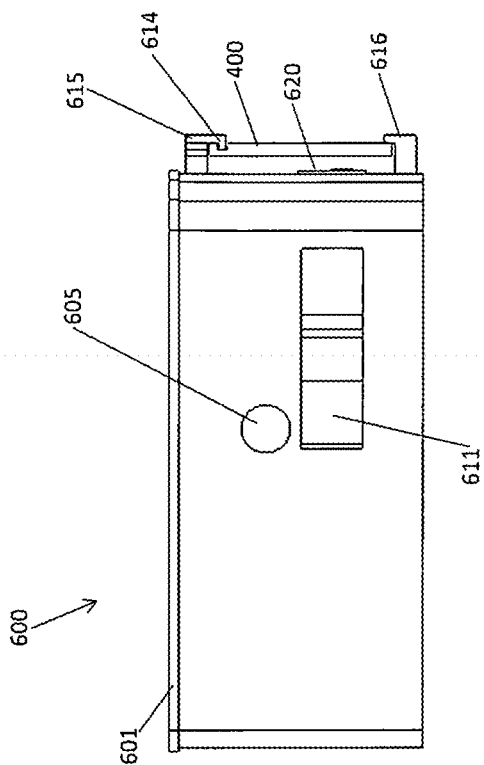
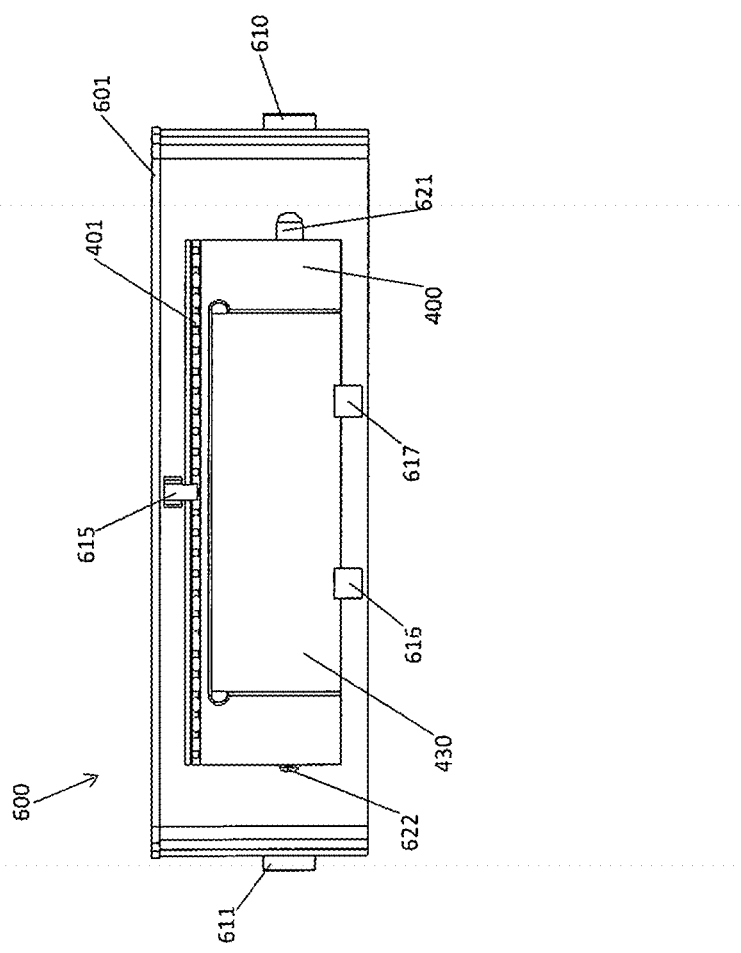
FIG. 8D
FIG. 8C

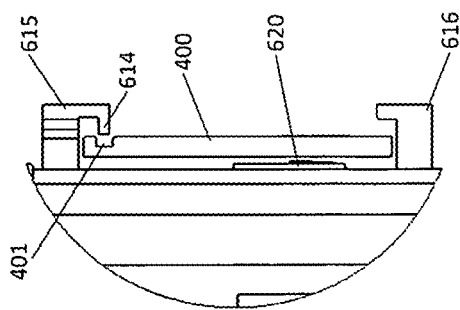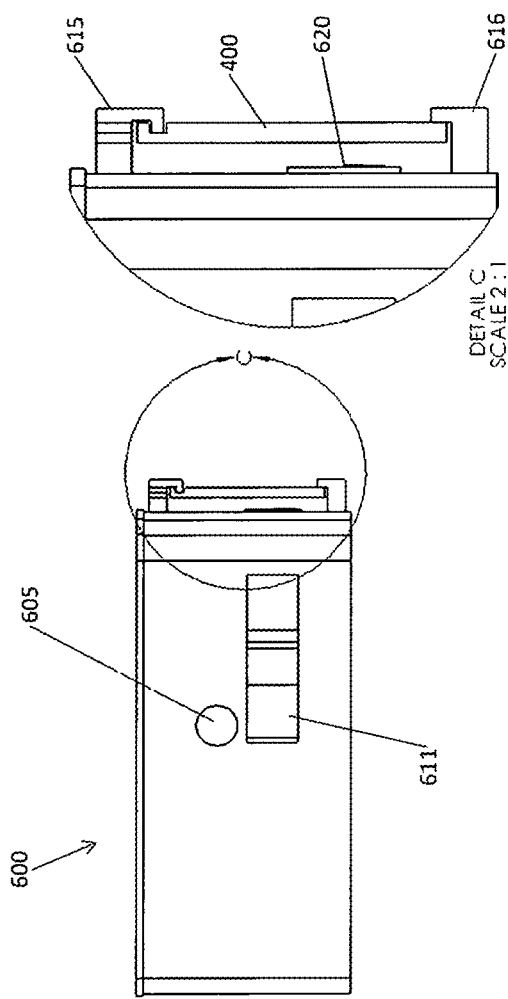
FIG. 10B
FIG. 10A

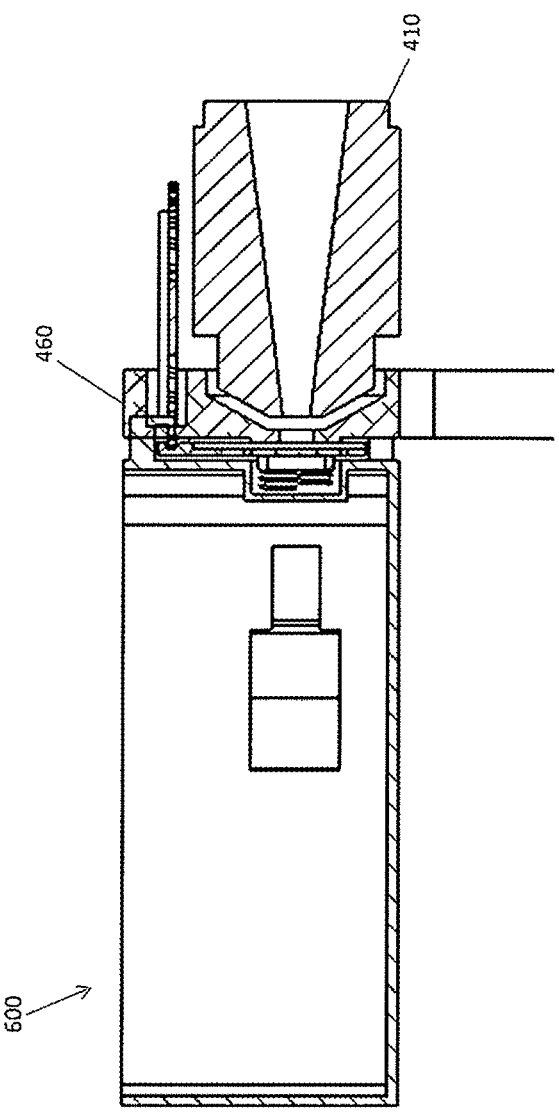
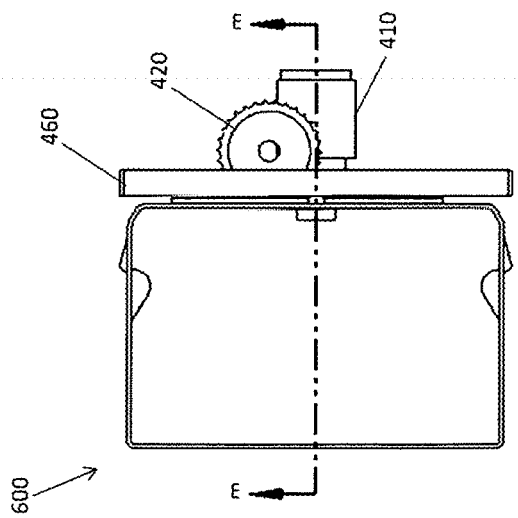
FIG. 10D
FIG. 10C

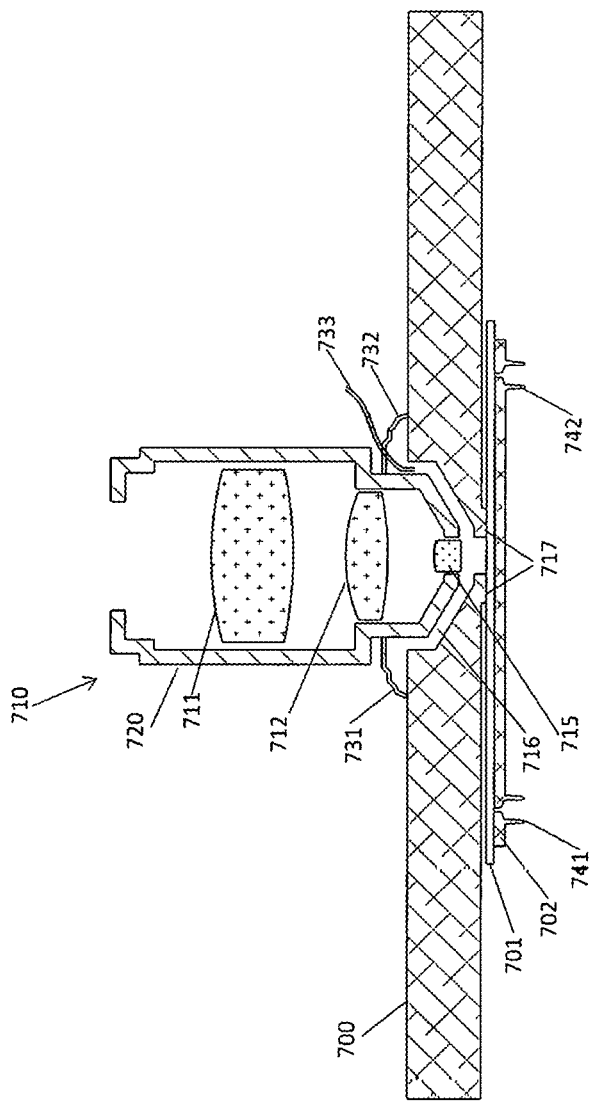

SCANNING APPARATUS AND METHOD USEFUL FOR DETECTION OF CHEMICAL AND BIOLOGICAL ANALYTES

CROSS REFERENCE TO RELATED APPLICATION

This application claims priority to U.S. Provisional Application No. 62/545,606 filed on Aug. 15, 2017 and entitled "SCANNING APPARATUS AND METHODS USEFUL FOR DETECTION OF CHEMICAL AND BIOLOGICAL ANALYTES," the disclosure of which is incorporated herein by reference in its entirety.

BACKGROUND

The present disclosure relates generally to detection of chemical and biological analytes and has specific applicability to nucleic acid sequencing.

The determination of nucleic acid sequence information is important in biological and medical research. Sequence information is used for identifying gene associations with diseases and phenotypes, identifying potential drug targets, and understanding the mechanisms of disease development and progress. Sequence information is an important part of personalized medicine, where it can be used to optimize the diagnosis, treatment, or prevention of disease for a specific individual.

Many scientists and medical practitioners struggle to tap into modern sequencing technology due to prohibitive costs to run and maintain complex instrumentation in current commercial offerings. These platforms favor centralized laboratories in which expensive "factory scale" instruments are run by highly trained specialists, and samples are batched to achieve economies of scale. This centralized system offers very little flexibility in terms of performance specifications—users are forced into ecosystems that are unnecessarily limited in scope and variety of use. When it comes to clinical applications, the centralized model is costly for doctors and their patients in terms of both the time and money required to ship patient samples from local clinics to distant sequencing labs. Further delays can be incurred as a centralized sequencing lab waits to receive sufficient number of samples to batch together into an economical run. Other applied markets such as forensics, veterinary diagnostics, food safety, agricultural analysis and environmental analysis suffer similar limitations.

Thus, there is a need for a sequencing platform that is better suited for use in local laboratories in support of a decentralized system of research and clinical care. The present invention satisfies this need and provides related advantages as well.

BRIEF SUMMARY

The present disclosure provides a detection apparatus that can include (a) a vessel having a lumen and a wall, wherein the wall has an internal surface and an external surface, wherein the internal surface contacts the lumen; (b) a reference surface that forms a structural loop with a detector; (c) a preload configured to urge the external surface of the vessel to contact an area on the reference surface; (d) a scan actuator configured to slide the vessel along the reference surface in a scan dimension; and (e) a transmitter configured to direct, to the detector, a signal from the internal surface or the lumen, when the external surface of the vessel is urged by the preload to contact the reference surface.

Also provided is a method of scanning a vessel. The method can include (a) translating a vessel along a reference surface of a detection apparatus, wherein the vessel comprises a lumen and a wall, wherein the lumen comprises analytes, wherein the reference surface contacts at least a portion of the vessel during the translating, and wherein the reference surface forms a structural loop with a detector; and (b) detecting the analytes at different locations along the vessel using the detector, wherein the vessel is urged to the reference surface by a preload during the detecting, thereby scanning the vessel.

In some embodiments, a method of scanning a vessel can include (a) examining a first subset of analytes in a vessel while applying a preload to a first portion of the vessel, wherein the preload positions the first subset of analytes to occupy an xy plane in a detection zone, wherein the preload is not applied to a second portion of the vessel; (b) translating the vessel to position a second subset of the analytes in the xy plane of the detection zone; and (c) examining the second subset of the analytes in the vessel while applying the preload to a second portion of the vessel, wherein the preload positions the second subset of the analytes to occupy the xy plane of the detection zone, wherein the preload is not applied to the first portion of the vessel, thereby scanning the vessel.

The present disclosure provides reactor apparatus. A reactor apparatus can include (a) a vessel having a lumen and a wall, wherein the wall has an internal surface and an external surface, wherein the internal surface contacts the lumen; (b) a reference surface that forms a structural loop with an energy source; (c) a preload configured to urge the external surface of the vessel to contact an area on the reference surface; (d) a scan actuator configured to slide the vessel along the reference surface in a scan dimension; and (e) a transmitter configured to direct energy from the energy source to the internal surface or the lumen when the external surface of the vessel is urged by the preload to contact the reference surface.

Also provided is a method of performing reactions in a vessel. The method can include (a) translating a vessel along a reference surface of a reactor apparatus, wherein the vessel comprises a lumen and a wall, wherein the lumen comprises reactants, wherein the reference surface contacts at least a portion of the vessel during the translating, and wherein the reference surface forms a structural loop with an energy source; and (b) directing energy from the energy source to the reactants at different locations along the vessel, wherein the vessel is urged to the reference surface by a preload during the directing of the energy to the reactants, thereby performing reactions in the vessel.

A method of performing reactions in a vessel can include (a) delivering energy from a reactor apparatus to a first subset of reactants in a vessel while applying a preload to a first portion of the vessel, wherein the preload positions the first subset of reactants to occupy an xy plane of a reaction zone, wherein the preload is not applied to a second portion of the vessel; (b) translating the vessel to position a second subset of the reactants in the xy plane of the reaction zone; and (c) delivering energy from the reactor apparatus to the second subset of the analytes in the vessel while applying the preload to a second portion of the vessel, wherein the preload positions the second subset of the analytes to occupy the xy plane, wherein the preload is not applied to the first portion of the vessel, thereby performing reactions in the vessel.

In particular embodiments, the present disclosure provides a detection apparatus that includes (a) a vessel having a lumen and a wall, wherein the wall has an internal surface and an external surface, wherein the internal surface contacts the lumen, and wherein the external surface has length l in a scan dimension x; (b) a reference surface; (c) a preload configured to urge the external surface of the vessel to contact an area on the reference surface, optionally the area of contact can have a maximum length in the scan dimension x that is shorter than length l; (d) a scan actuator configured to slide the vessel along the reference surface in the scan dimension x; (e) a detector; and (f) an objective configured to direct radiation from the vessel to the detector when the external surface of the vessel is urged by the preload to contact the reference surface.

Also provided is a method of optically scanning a vessel. The method can include (a) providing a vessel having a lumen and a wall, wherein the lumen contains optically detectable analytes and wherein the wall is transparent to the optically detectable analytes; (b) translating a length of the vessel along a reference surface and detecting the optically detectable analytes at different locations along the length, wherein the reference surface contacts only a portion of the length of the vessel at any time during the translation, wherein the vessel is urged to the reference surface by a preload during the detection, wherein the detection includes transmitting radiation through the wall, then through an objective and then to a detector, thereby optically scanning the vessel.

The present disclosure further provides a detection apparatus that includes (a) a vessel having a lumen and a wall, wherein the wall has an internal surface and an external surface, wherein the wall has a plurality of discrete contacts between the internal surface and the external surface, wherein the internal surface contacts the lumen, and wherein the plurality of discrete contacts occupies a length l in a scan dimension x; (b) a transmissive surface; (c) a preload configured to urge discrete contacts on the external surface of the vessel to contact the transmissive surface, optionally the area of the transmissive surface can have a maximum length in the scan dimension x that is shorter than length l; (d) a scan actuator configured to slide the vessel along the transmissive surface in the scan dimension x; and (e) a detector configured to acquire signals from the discrete contacts via the transmissive surface.

BRIEF DESCRIPTION OF THE DRAWINGS

FIG. 2A shows an exploded, profile view of a flow cell and detection apparatus;

FIG. 2B shows a profile view of the flow cell in contact with a detection apparatus;

FIG. 6A and FIG. 6B show front and rear perspective views of a ball screw mechanism for translating a flow cell relative to a detection apparatus.

FIG. 8A shows a perspective view of a fluidic caddy with an attached flow cell;

FIG. 8B shows an expanded view of the attachment points for the flow cell to the caddy;

FIG. 8C shows a front view of the fluidic caddy with attached flow cell;

FIG. 8D shows a side view of the fluidic caddy with attached flow cell;

FIG. 10A shows a side view, and expanded view of section c, for a fluidic caddy with attached flow cell;

FIG. 10B shows the expanded view of the flow cell after being released from the fluidic caddy;

FIG. 10C shows a top view of a fluidic caddy engaged with components of a detection apparatus;

FIG. 10D shows a cutaway view of the fluidic caddy (along line m) engaged with components of a detection apparatus.

FIG. 11 shows a cutaway profile view of a rigid support aligned to a flow cell and an immersion objective.

DETAILED DESCRIPTION

Figure 1:
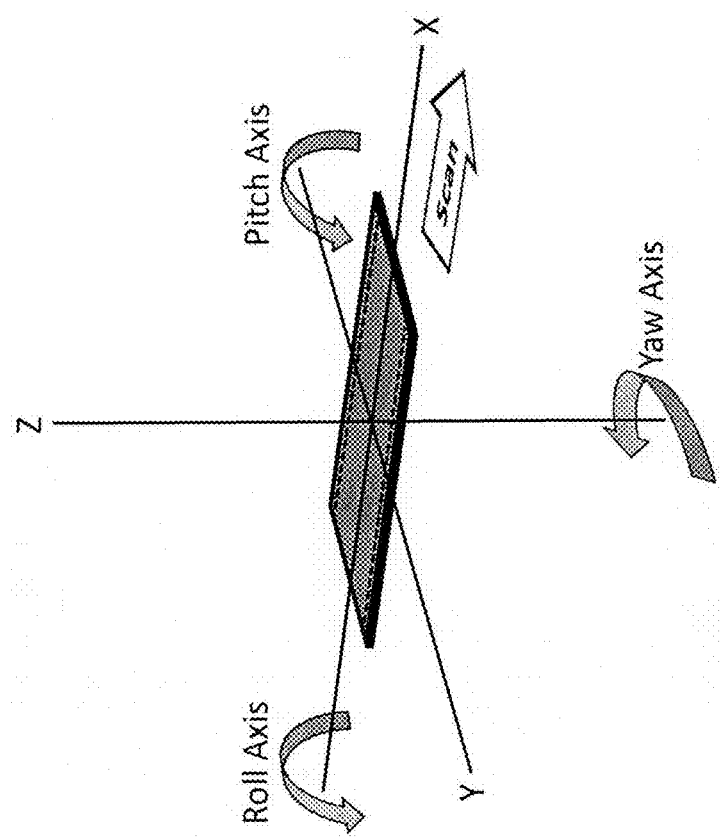
FIG. 1 shows dimensions and axes of rotation used to describe relative orientation of components in optical systems and other apparatus set forth herein.

The present disclosure provides apparatus and methods for detecting analytes, such as chemical or biological analytes. The detection can occur for analytes that are consumed, modified or produced as part of a reaction of interest. Several embodiments of the apparatus and methods are well suited to detection of repetitive reactions such as those used to characterize or synthesize polymers. A wide variety of polymers exist in nature and an infinite variety of polymers can be made by natural processes, or synthetic processes that nevertheless utilize a relatively small number of monomeric building blocks. For example, DNA is synthesized in nature from four different nucleotides, as is RNA. Protein, another ubiquitous polymer, is made from 20 different genetically encoded amino acids. Apparatus and methods of the present disclosure can be configured to sequentially detect monomeric building blocks, thereby providing a capability to identify any sequence. In particular embodiments, the apparatus and methods can be configured to detect analytes that are consumed, produced or modified during a multi-cycle, repetitive reaction process. For example, intermediate products can be detected at each individual cycle. By way of more specific example, nucleic acids can be sequenced by serially delivering reagents that specifically react with, or bind to, the four different types of nucleotide monomers, and components of each reaction (e.g. labeled nucleotides or labeled polymerases) can be detected during or after each cycle. Alternatively, nucleic acids can be synthesized by serially delivering one of four different nucleotide monomers, or precursors thereof, in a predefined order to a growing polymer and then products (e.g. blocking moieties released during deprotection) can be detected for each cycle. Sequencing or synthesis of proteins can also be detected cyclically using apparatus and methods set forth herein.

Various aspects of the present invention are exemplified with regard to scanning detection. It will be understood that apparatus and methods set forth herein can be used for precise spatially resolved manipulation of reagents or substrates in a vessel whether or not the reagents or substrates are detected. For example, light energy can be delivered to a vessel to perform photoreactions at spatially resolved locations in a vessel or to fabricate light responsive materials in a spatially resolved manner.

This disclosure provides apparatus and methods that can be used to observe a vessel by translational movement of the vessel relative to a detector. Also provided are apparatus and methods to address a vessel, for example, by delivery of localized energy, by translational movement of the vessel relative to an energy source. When detecting analytes, this scanning motion allows the detector to collect signals from sequential subsections of the vessel. The collective combination of signals sums to a total field of detection that is larger than the static detection field of the detector. Taking, for example, a vessel having an interior surface to which an array of optically labeled analytes is attached, translation of the vessel relative to an optical detector can provide an image of the array that is larger than the field of view of the detector. Similarly, scanning-based delivery of energy can allow sequential reactions to be carried out in a vessel.

A difficulty that plagues many scanning detectors is that mechanisms for translating the vessel relative to the detector are coupled with mechanisms for adjusting rotational registration of the vessel with respect to the detector. As such, the scanning detector is burdened with a tolerance stack that includes not only translational tolerances but also rotational tolerances. Relatively small amounts of rolling rotation or pitching rotation (i.e. rotation around the x axis and rotation around the y axis, respectively, as diagrammed in FIG. 1) can have significant adverse impacts on high resolution imaging of an analyte array. This adverse impact is exacerbated in optical scanning applications since a small pitch deviation (i.e. rotation around the y axis) will manifest as an increasing drift out of focus as the optical detector scans a vessel along the x dimension. The longer the scan, the further the deviation from focus.

A common solution to the problem of high tolerance stacks in optical scanners has been to employ moving stages having high precision actuators that are adjustable in a variety of translational and rotational directions. High precision actuators add cost and complexity to a scanner, and such rigs typically require highly trained technicians for routine maintenance. Particular embodiments of the apparatus and methods set forth herein avoid these problems by decoupling the mechanism that is used to translate a vessel with respect to a detector from the mechanism that is used to rotationally register the vessel with respect to the detector. Decoupling translation from rotational registration reduces the tolerance stack for the translation mechanism in detection apparatus and other apparatus of the present disclosure.

A further advantage of replacing a typical stage with a vessel translation apparatus of the present disclosure is that the vessel can be scanned more quickly. The increase in scanning speed is, in large part, a function of the vessel translation apparatus being configured to move a mass that is smaller than a typical stage. A small mass takes less time to settle compared to a larger mass that is moved the same distance. For example, the time spent waiting for a vessel to settle prior to acquiring an image becomes increasingly significant as the desired resolution for detection increases because the motion of the vessel must dampen to a point that the average displacement experienced by features of the object under observation is small enough to preclude substantial distortions in the image. Taking as an example a typical nucleic acid sequencing apparatus, DNA is present in sites of an array that are only a few microns apart and that are observed at low micron resolution. A typical stage used to move the array for sequencing requires settle times of several hundred milliseconds to dampen to the point that displacements are less than a few microns. Avoiding a typical stage by using an apparatus of the present disclosure allows settle times on the order of a few tens of milliseconds. The milliseconds can add up to hours for a nucleic sequencing protocol or other repetitive scanning operation. For example, saving 500 hundred milliseconds per image adds up to a savings of about 4 hours in settling time alone for a sequencing protocol that acquires 200 images per cycle and performs 150 cycles per run. Similar improvements in processing speed can be achieved for other scanning applications such as photochemistry, photolithography, microfabrication or nanofabrication (e.g. via laser etching), laser ablation or the like.

Although apparatus and methods set forth herein provide advantages in reducing settle time, it will be understood that the uses need not be limited to processes that include a settling step. Accordingly, apparatus and methods set forth herein in the context of so called "step and shoot" scanning procedures can be applied to continuous scanning operations such as time delayed integration (TDI) scanning. For example, apparatus and methods set forth herein can be modified for use in TDI line scanning operations such as those set forth in U.S. Pat. No. 7,329,860, which is incorporated herein by reference.

As set forth in further detail herein, rotational registration of a vessel with respect to a detector can be achieved by physically contacting the vessel with a reference surface, the reference surface being rotationally fixed with respect to the detector. In particular embodiments, as exemplified below, a vessel can be compressed to the reference surface by a preload. Separately, translation can be achieved by a scan actuator (e.g. a gear) that interacts directly with another surface of the vessel (e.g. a rail that complements the gear). The preload and scan actuator need not interact to achieve motion and registration of the vessel. For example, the preload need not be applied to the vessel while the vessel is being translated. However, interaction between the preload and scan actuator can occur for certain applications of the apparatus and methods set forth herein. Accordingly, the preload can be applied to the vessel while the vessel is being translated.

In some embodiments, a vessel that is to be detected can be a component of a cartridge. The cartridge can provide a convenient mechanism to deliver the vessel to a detector. For example, a detector can be maintained inside of an analytical instrument to protect the detector from environmental factors such as moisture, dust or light. A cartridge can be introduced to the analytical instrument via a door or opening such that the vessel is contacted with the detector. In some embodiments, the analytical instrument will remove the vessel from the cartridge and translate the vessel past the detector in a way that does not necessarily involve movement of the cartridge. Alternatively, the vessel can maintain contact with the cartridge such that both the cartridge and vessel are moved to achieve translation or scanning. In a further alternative, the cartridge can be a component of the analytical instrument and the vessel can be introduced to the instrument by placing the vessel into the cartridge.

Alternatively and/or additionally, the vessel can be a component of a caddy that also includes reservoirs and fluidic components that deliver reagents to the vessel during the course of a reaction that is detected, such as a nucleic acid sequencing reaction. In some embodiments, the caddy includes sufficient fluidic components that it functions as a "wet" component and the analytical instrument housing the detector functions as a "dry" component. An advantage of having separate wet and dry components is that the caddy and vessel can be dedicated to a particular sample or reaction, and when the reaction is complete, the caddy and vessel can be removed from the analytical instrument and replaced with a new caddy and vessel dedicated to a second sample or reaction. Because the samples, reagents and reaction products for each of these two reactions are physically separated from the analytical instrument, cross contamination between the reactions, that would otherwise cause detection artifacts, are avoided.

The physical separation of the components provides a further advantage of avoiding unnecessary downtime for the analytical instrument if the fluidic component experiences mechanical difficulties. Specifically, unlike many commercially available analytical instruments which have permanently integrated fluidics, a fluidic system failure can be conveniently overcome by merely removing a faulty fluidic caddy and replacing it with another so that the analytical instrument experiences little to no downtime. In some embodiments, the caddy is disposable, for example, being made from relatively inexpensive components. The caddy can be configured in a way that reagents are sealed in the caddy thereby avoiding unwanted contamination of the environment and unwanted exposure of laboratory personnel and equipment to the reagents. Alternatively, the fluidics caddy can be emptied, refilled and re-used if desired for a particular application.

In some embodiments, a fluidic caddy of the present disclosure includes not only reagent reservoirs, but also includes one or more waste reservoirs. Reagent that is not consumed in a reaction and/or unwanted products of a reaction can be collected in the waste reservoir. Advantages of retaining pre- and post-reaction fluids in a caddy include convenience of the user in handling a single fluidic component before and after a reaction is performed, minimizing user contact with chemical reagents, providing a compact footprint for the apparatus and avoiding unnecessary proliferation of fluid containers.

Exemplary fluidic caddies, reaction vessels and fluidic components that can be modified, in accordance with teachings herein, for use in combination with detection components of the present disclosure are described in commonly owned U.S. patent application Ser. No. 15/922,661, which claims the benefit of U.S. Provisional App. No. 62/481,289, each of which is incorporated herein by reference. Other fluidic components that are useful, particularly for cyclic reactions such as nucleic acid sequencing reactions, are set forth in US Pat. App. Pub. Nos. 2009/0026082 A 1; 2009/0127589 A 1; 2010/0111768 A 1; 2010/0137143 A1; or 2010/0282617 A1; or U.S. Pat. Nos. 7,329,860; 8,951,781 or 9,193,996, each of which is incorporated herein by reference.

The details of one or more embodiments are set forth in the accompanying drawings and the description below. The drawings and description are provided as examples for purposes of explanation and are not necessarily intended to limit the scope of the invention. The invention is susceptible to modifications in the methods and materials, as well as alterations in the fabrication methods and equipment. Such modifications will become apparent to those skilled in the art from a consideration of the drawings and the description below.

The present disclosure provides a detection apparatus. The apparatus can include (a) a vessel having a lumen and a wall, wherein the wall has an internal surface and an external surface, wherein the internal surface contacts the lumen; (b) a reference surface that forms a structural loop with a detector; (c) a preload configured to urge the external surface of the vessel to contact an area on the reference surface; (d) a scan actuator configured to slide the vessel along the reference surface in a scan dimension; and (e) a transmitter configured to direct, to the detector, a signal from the internal surface or the lumen, when the external surface of the vessel is urged by the preload to contact the reference surface.

In particular embodiments, a detection apparatus can include (a) a vessel having a lumen and a wall, wherein the wall has an internal surface and an external surface, wherein the internal surface contacts the lumen, and wherein the external surface has length l in a scan dimension x; (b) a reference surface; (c) a preload configured to urge the external surface of the vessel to contact an area on the reference surface, optionally the area of contact can have a maximum length in the scan dimension x that is shorter than length l; (d) a scan actuator configured to slide the vessel along the reference surface in the scan dimension x; (e) a detector; and (f) an objective configured to direct radiation from the vessel to the detector when the external surface of the vessel is urged by the preload to contact the reference surface.

The present disclosure also provides is a method of scanning a vessel. The method can include (a) translating a vessel along a reference surface of a detection apparatus, wherein the vessel comprises a lumen and a wall, wherein the lumen comprises analytes, wherein the reference surface contacts at least a portion of the vessel during the translating, and wherein the reference surface forms a structural loop with a detector; and (b) detecting the analytes at different locations along the vessel using the detector, wherein the vessel is urged to the reference surface by a preload during the detecting, thereby scanning the vessel.

In some embodiments, a method of scanning a vessel can include (a) examining a first subset of analytes in a vessel while applying a preload to a first portion of the vessel, wherein the preload positions the first subset of analytes to occupy an xy plane in a detection zone, wherein the preload is not applied to a second portion of the vessel; (b) translating the vessel to position a second subset of the analytes in the xy plane of the detection zone; and (c) examining the second subset of the analytes in the vessel while applying the preload to a second portion of the vessel, wherein the preload positions the second subset of the analytes to occupy the xy plane of the detection zone, wherein the preload is not applied to the first portion of the vessel, thereby scanning the vessel.

Also provided is a method of optically scanning a vessel. The method can include (a) providing a vessel having a lumen and a wall, wherein the lumen contains optically detectable analytes and wherein the wall is transparent to the optically detectable analytes; (b) translating a length of the vessel along a reference surface and detecting the optically detectable analytes at different locations along the length, wherein the reference surface contacts only a portion of the length of the vessel at any time during the translation, wherein the vessel is urged to the reference surface by a preload during the detection, wherein the detection includes transmitting radiation through the wall, then through an objective and then to a detector, thereby optically scanning the vessel.

FIG. 2 shows an exemplary arrangement for scanning a vessel relative to a detector. As shown in the profile views of FIG. 2A and FIG. 2B, the vessel is a flow cell 101 that is aligned with objective 110 via a rigid body 100. The back side of rigid body 100 has a conical depression 116 that complements the shape of objective 110. Accordingly, objective 110 can be moved close to the flow cell for a desired focus or resolution. Any of a variety of depression shapes can be used as desired to accommodate the shapes for various objectives or other optical components. The front side of rigid body 100 has a reference surface 117 that will contact a planar face of flow cell 101. The flow cell 101 is maintained in contact with the reference surface 117 by a preload that applies positive pressure to the side of flow cell 101 that is opposite the reference surface 117. The preload is formed by compression foot 102 which contacts flow cell 101 under force of spring 103.

Generally, reference surface 117 and compression foot 102 create low friction contacts with flow cell 101. This allows the flow cell to slide past the reference surface 117 and to slide past compression foot 102 while under compression force of the preload. This compression provides alignment of the flow cell 101 with the objective 110 via the rigid body throughout the course of flow cell 101 scanning by the objective 110. The reference surface and objective are components of a structural loop. The structural loop contains structural elements that locate the vessel (e.g. flow cell) with respect to the detector (e.g. via the objective). Because the reference surface is pre-aligned with the objective, compressing the flow cell to the reference surface prevents unwanted pitch and roll of the flow cell with respect to the objective. Components of FIG. 2 that are in the structural loop include reference surface 117, which is connected to rigid body 100, which is connected to base 114. Base 114 can be connected to a plate or other structural element that is physically connected to components of an optical system such as those exemplified in FIG. 9.

In the example shown in FIG. 2, reference surface 117 is polished aluminum, which provides rigidity for aligning the flow cell 101 to the objective 110 and a low friction surface for sliding the glass surface of the flow cell 101. Any of a variety of materials can be used that provide rigidity and low friction for the reference surface including, for example, acetal resins (e.g. Delrin® available from DuPont, Wilmington, Del.), diamond like carbon or polished metals. The compression foot 102 provides a low friction surface for the sliding translation of the flow cell 101 glass surface and also provides compressibility to form a compliant contact with the flow cell 101 under the force of spring 103. Any of a variety of materials can be used that provide low friction to the compression foot including, for example, those set forth above for reference surface 117. Optionally, a low friction material used in an apparatus herein can also be compressible, examples of which include, but are not limited to, polytetrafluoroethylene (PTFE, Teflon®), perfluoroalkoxy alkane (PFA), fluorinated ethylene propylene (FEP), silicone foam, nitrile rubber, Buna-N, Perbunan, acrylonitrile butadiene rubber or nitrile butadiene rubber (NBR). Alternatively or additionally, low friction can be achieved using ball bearings, rollers and/or lubricating fluids. Typically, the lubricating fluid is used on the side of the flow cell that is not between the analytes and detector or a fluid is used that does not interfere with detection. In some embodiments, lubricating fluids are not present at the interface between the reference surface and the exterior surface of the vessel wall. For example, lubricating fluids can be avoided to prevent interference caused when the fluid enters the area between the detector and vessel.

In particular embodiments, a vessel (or cartridge containing a vessel) is positioned in an xy plane without contacting a reference surface. For example, a vessel (or cartridge) can be urged, by a preload, toward a fluid bearing or magnetic bearing such that the combination of forces provided by the preload and bearing results in a desired positioning. A fluid bearing can be a gas bearing, whereby gas pressure provides a force for positioning the vessel (or cartridge). Another useful type of fluid bearing is a liquid bearing, whereby liquid pressure provides a force for positioning the vessel (or cartridge). The liquid can be selected for the ability to index match with optical components of the system, such as the wall of the vessel, so as to minimize aberrations when detecting optical signals or delivering radiation.

Figure 2D:
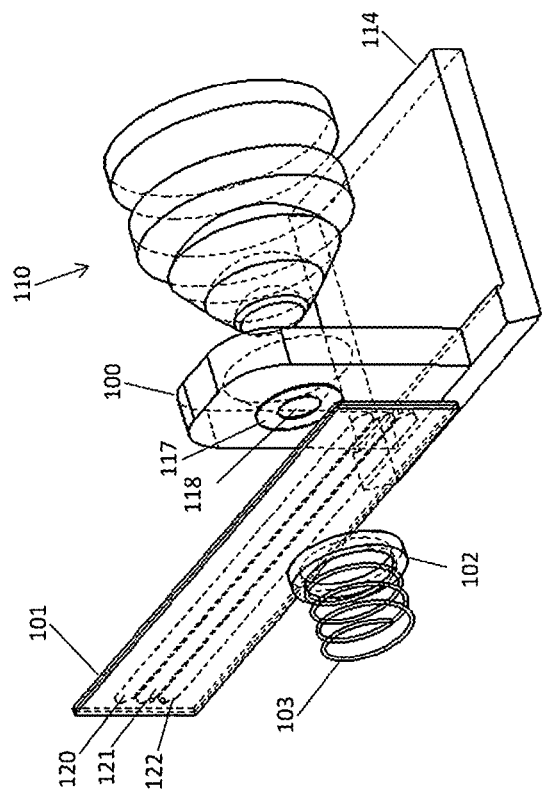
FIG. 2D shows an exploded, perspective view of the flow cell in contact with the detection apparatus.
Figure 2C:
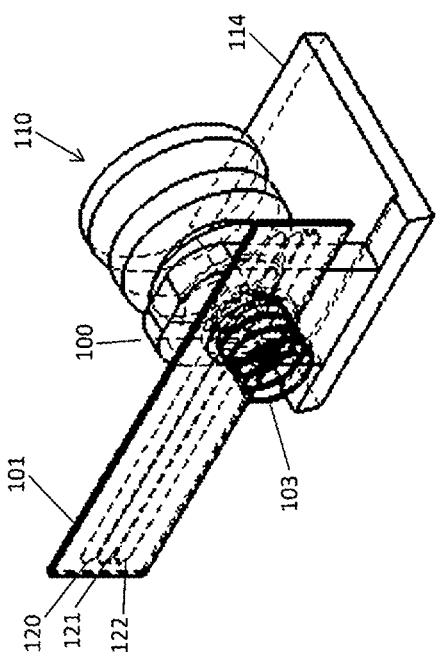
FIG. 2C shows a perspective view of the flow cell in contact with the detection apparatus.

As shown in FIG. 2C and FIG. 2D, reference surface 117 has a planar surface that forms a flat ring on the front face of rigid body 100. The ring is raised compared to the front face of rigid body 100. Raising the reference surface helps to prevent unwanted contact between the flow cell 101 and rigid body 100 that may otherwise create friction that hinders translation. Raising the reference surface 117 also isolates the area of the flow cell that is to be detected and prevents unwanted warping that could otherwise occur if the flow cell contacted other regions of rigid body 101. In the example of FIG. 2, the reference surface has an area that is smaller than the surface of the flow cell and thus only contacts a portion of the flow cell surface. However, in alternative embodiments, the reference surface can be substantially the same size or larger than the flow cell surface and thus can contact substantially all of the flow cell surface (optionally, excepting the area of the flow cell surface that is juxtaposed with a detection window, objective or other transmitter).

In the example shown, reference surface 117 surrounds circular window 118, this window being a hole through rigid body 100. Alternatively, circular window 118 can include a material that is capable of transmitting a signal that is to be detected. For example, the window can be made of quartz, glass, or plastic that facilitates transmission of signals that are to be detected. In some configurations, the window can contain an index matched immersion fluid that contacts the flow cell surface to facilitate detection, as set forth in further detail below with regard to FIG. 11. The circular window 118 is aligned with the front lens 115 of the objective 110 such that the objective 110 can observe flow cell 101 through the window 118. Compression foot 102 has a flat ring shape providing a footprint on flow cell 101 that is complementary to the footprint of flat ring 117 on the opposite side of the flow cell. In this example, the preload (via foot 102) has a contact area with the vessel (flow cell 101) that is the same as the area of contact between reference surface 117 and the vessel. Alternatively, the preload can have a contact area with the vessel that is smaller than the area of contact between the reference surface and the vessel. Indeed, the preload can have a contact area with the vessel that is no larger than the area of contact between the reference surface and the vessel.

Generally, complementarity between the footprints of the preload and reference surface can be configured to result in the compression foot 102 having a contact area on the flow cell 101 that excludes surface area of the flow cell opposite the circular window 118 and that further excludes surface area of the flow cell opposite the region of the rigid body that surrounds reference surface 117. Complementarity between the footprints of compression foot 102 and reference surface 117 helps to maintain flatness for the portion of the flow cell surface that is observed through window 118. This complementarity can be beneficial for detecting analytes on the inner surface of the flow cell, especially at high magnification and high resolution. The complementarity can also facilitate trans-illumination, whereby radiation can pass back or forth through a path defined by the hollow space in the spring 103, compression foot 102 and window 118. The circular shape of the reference surface and preload is exemplary. Other shapes can be used including, but not limited to, square, rectangular, polyhedral, elliptical, triangular or the like. Moreover, the shape need not be continuous. Instead the reference surface and/or contact surface for the preload can be a discontinuous area such as that formed by two parallel tracks or by interruptions to the above shapes. Particularly useful applications are nucleic acid microarray detection and nucleic acid sequencing. The shapes and orientations for preload and reference surface can be used for apparatus that deliver energy to a vessel or that detect non-optical signals.

As exemplified by FIG. 2, a particularly useful vessel for use in a detection apparatus or other apparatus of the present disclosure is a flow cell. Any of a variety of flow cells can be used including, for example, those that include at least one channel and openings at either end of the channel. The openings can be connected to fluidic components to allow reagents to flow through the channel. The flow cell is generally configured to allow detection of analytes within the channel, for example, in the lumen of the channel or on the inner surface of a wall that forms the channel. In some embodiments, the flow cell can include a plurality of channels each having openings at their ends. For example, the flow cell shown in FIG. 2 has three channels 120, 121 and 122 each having openings at both ends. Multiple channels can interact with a fluidic system via a manifold.

In particular embodiments, a flow cell will include a solid support to which one or more target analytes or reagents are attached. A particularly useful solid support is one having an array of sites. Arrays provide the advantage of facilitating multiplex detection. For example, different reagents or analytes (e.g. cells, nucleic acids, proteins, candidate small molecule therapeutics etc.) can be attached to an array via linkage of each different analyte to a particular site of the array. Exemplary array substrates that can be useful include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available array substrates that can be used include, for example, an Affymetrix GeneChip™ array. A spotted array substrate can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful array substrates include those that are used in nucleic acid sequencing applications. For example, arrays that are used to create attached amplicons of genomic fragments (often referred to as clusters) can be particularly useful. Examples of substrates that can be modified for use herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

An array can have sites that are separated by less than 100 µm, 50 µm, 10 µm, 5 µm, 1 µm, or 0.5 µm. In particular embodiments, sites of an array can each have an area that is larger than about 100 µm$^2$, 250 µm$^2$, 500 µm$^2$, 1 µm$^2$, 2.5 µm$^2$, 5 µm$^2$, 10 µm$^2$, 100 µm$^2$, or 500 µm$^2$. Alternatively or additionally, sites of an array can each have an area that is smaller than about 1 mm$^2$, 500 µm$^2$, 100 µm$^2$, 25 µm$^2$, 10 µm$^2$, 5 µm$^2$, 1 µm$^2$, 500 µm$^2$, or 100 µm$^2$. Indeed, a site can have a size that is in a range between an upper and lower limit selected from those exemplified above. An array can have sites at any of a variety of densities including, for example, at least about 10 sites/cm$^2$, 100 sites/cm$^2$, 500 sites/cm$^2$, 1,000 sites/cm$^2$, 5,000 sites/cm$^2$, 10,000 sites/cm$^2$, 50,000 sites/cm$^2$, 100,000 sites/cm$^2$, 1,000,000 sites/cm$^2$, 5,000,000 sites/cm$^2$, or higher. An embodiment of the apparatus or methods set forth herein can be used to image an array at a resolution sufficient to distinguish sites at the above densities or site separations.

Several embodiments utilize optical detection of analytes in a flow cell. Accordingly, a flow cell can include one or more channels each having at least one transparent window. In particular embodiments, the window can be transparent to radiation in a particular spectral range including, but not limited to x-ray, ultraviolet (UV), visible (VIS), infrared (IR), microwave and/or radio wave radiation. In some cases, analytes are attached to an inner surface of the window(s). Alternatively or additionally, one or more windows can provide a view to an internal substrate to which analytes are attached. Exemplary flow cells and physical features of flow cells that can be useful in a method or apparatus set forth herein are described, for example, in US Pat. App. Pub. No. 2010/0111768 A1, WO 05/065814 or US Pat. App. Pub. No. 2012/0270305 A1, each of which is incorporated herein by reference in its entirety.

Several examples herein are demonstrated for a rectangular flow cell 101 having elongated channels. In these examples, the area of contact between the flow cell 101 and reference surface 117 has a maximum length in the scan dimension x that is shorter than the length of the flow cell lane in scan dimension x. More specifically, the diameter of ring 117 is shorter than the length of lanes 120, 121 or 122. Alternatively or additionally, the area of contact between the flow cell 101 and reference surface 117 can have a maximum width w in dimension y that is shorter than the width of the flow cell lane in dimension y. Specifically, the diameter of ring 117 can be shorter than the width of any one of lanes 120, 121 or 122.

Similarly, the maximum diameter or length of window 118 in the scan dimension x can be shorter than the length of the flow cell lane in the scan dimension x. Alternatively or additionally, the maximum diameter or width of window 118 in the y dimension can be shorter than the width of any one of lanes 120, 121 or 122. In this configuration, the complete width of the lane can be observed by translation in the y direction. In some embodiments, the area of window 118 and width of the lane can be configured so that translation in the y dimension is not necessary to observe the entire width of the lane. For example, the area of window 118 can have a maximum diameter or width w in dimension y that is equivalent to or longer than the width of the flow cell lane in dimension y.

In particular embodiments a vessel, such as a flow cell, can be moved in an arcuate path during all or part of a scanning operation. Looking to the flow cell orientation in FIG. 1, the arcuate path can result from rotation around the yaw axis. The arcuate path can be a circle, spiral or other path that is desirable for scanning a vessel. Optionally, the area of contact between a vessel and reference surface can have a length or area that is smaller than the length or area, respectively, of the arcuate path. By way of more specific example, a ring-shaped reference surface can have a diameter that is shorter than the length of the arcuate path or shorter than the length of a lane in a flow cell that is moved along the arcuate path. Similarly, the maximum diameter or area of a window in the reference surface, through which detection occurs, can be smaller than the length or area, respectively, of the arcuate path; or the window can be smaller than a flow cell lane that is scanned along an arcuate path.

A flow cell need not be rectangular in shape. Alternative shapes that can be used include, but are not limited to, a disc, square, polygon or irregular shape. The lanes of a flow cell can follow a linear path, arcuate path, winding path or the like. Other types of vessels can also be used. For example, a well of a multi-well strip or multi-well plate can be detected using an apparatus or method of the present disclosure. The bottom surface of a well can be urged toward a reference surface by a preload applied to the top of the vessel (e.g. by contacting a compression foot to the upper side of a multi-well plate or multi-well strip). Optionally, the well can have a flat bottom that contacts the reference surface. As a further option, the well will be larger than the field of view of the detector. For example, the well may be circular in shape and may have a diameter l in scan dimension x that is longer than the length of the reference surface in the scan dimension x.

Another exemplary vessel type is a cylindrical- or tube-shaped vessel such as a capillary tube. The body of a tube can be held to a reference surface under the force of a preload as exemplified herein for flat shaped vessels. In an exemplary configuration the length of the tube can be parallel to the scan axis such that scanning the tube along x will result in relative motion of the reference surface along the length of the tube. For a tube that is configured in this orientation, it may also be useful to rotate the tube in the roll axis. This rotation will result in relative motion of the reference surface around the circumference of a section of the tube. Combining translation along x and rotation along the roll axis can allow a substantial surface area of the tube to come into contact with the reference surface. For example, the tube and reference surface can move in a helical or spiral path relative to each other. The reference surface can be flat, as exemplified herein for flow cells having a flat exterior wall. Alternatively, the reference surface can have a curved shape (e.g. u-shaped or saddle-shaped cross section) that accommodates and orients a cylindrical- or tube-shaped vessel that it contacts.

Typically, the vessel wall is made from a rigid material that is not readily flexible under the conditions used. In alternative embodiments, a vessel is made from a flexible material, for example, forming a sheet, tape, belt or ribbon that can be passed along a reference surface and detected while the vessel is under the urging of a preload. For example, a plurality of analytes, such as an array of nucleic acids, can be attached to the surface of the flexible material and detected when in contact with the reference surface. Exemplary, flexible materials having attached analytes are described, for example, in U.S. Pat. No. 9,073,033 and US Pat. App. Pub. No. 2016/0076025 A1, each of which is incorporated herein by reference.

When using a vessel having a flexible wall, it may be advantageous to pull the wall material over a reference surface, for example, to stretch or straighten the portion of the wall material that is observed by a detector. For example, the reference surface can be a raised rim that surrounds a detection window and the flexible material can be pulled over the rim to apply a pulling force across the window. Pulling can be achieved for example by applying suction to the flexible material via a vacuum chuck that surrounds the raised rim. Suction can be applied as an alternative or supplement to other preload mechanisms set forth herein.

As will be evident from the examples set forth herein, a vessel can be open (e.g. a well of a multi-well plate, surface of a chip, or surface of a sheet) or the vessel can be enclosed (e.g. a lane of a flow cell). It will be understood that, wells of a multi-well plate can optionally be covered to create an enclosed vessel and similarly a sheet, belt, tape or ribbon can have multiple layers such that an internal lumen occurs between layers. Alternatively, a vessel can have one or more open structures such as a trough, well or other concave structure that contains a fluid. A vessel can also have a convex or protruding structure such as a post or ridge, and optionally individual protrusions can each be attached to one or more analyte that is to be detected or manipulated.

The preload exemplified in FIG. 2 creates a pushing force on the side of the vessel (e.g. flow cell) that is opposite the side of the vessel that contacts the reference surface. Pushing force can derive from a spring, clamp, positive air pressure, positive fluid pressure, charge repulsion, charge attraction, magnetic attraction or magnetic repulsion. Alternatively, a preload can be configured to create a pulling force on the vessel. For example, a magnetic or ferromagnetic material that is in or on the vessel can be attracted to the reference surface, or charges in or on the vessel can be attracted to the reference surface. In this example, the reference surface or area surrounding the reference surface can contain magnetic or ferromagnetic material that acts as a preload. In another embodiment, pulling force can result from a vacuum chuck that is configured to apply suction to an area of the vessel that contacts the reference surface. In a further embodiment, a magnetic clamping force can be used, whereby the vessel is sandwiched between a magnetic or ferromagnetic material on or around the reference surface that attracts a magnetic or ferromagnetic body that is external to the opposite side of the vessel.

A detection apparatus or other apparatus of the present disclosure can include a scan actuator that is configured to slide a vessel along a reference surface. The vessel can slide along the reference surface and along the surface of the preload. Generally, the scan actuator is configured to move the vessel while the vessel is in contact with the reference surface under the urging of a preload. However, it is also possible to translate the vessel without simultaneously applying a preload to the vessel. It is also possible to translate the vessel through a space defined by a bearing that does not physically contact the vessel, such as a fluid bearing or magnetic bearing. For example, a vessel can be positioned via opposing forces of a preload against a bearing. Particularly useful actuators employ one or more gears that interact with perforations or threads on a flow cell or on a cartridge that contains the flow cell. Several examples are set forth below.

Figure 3B:
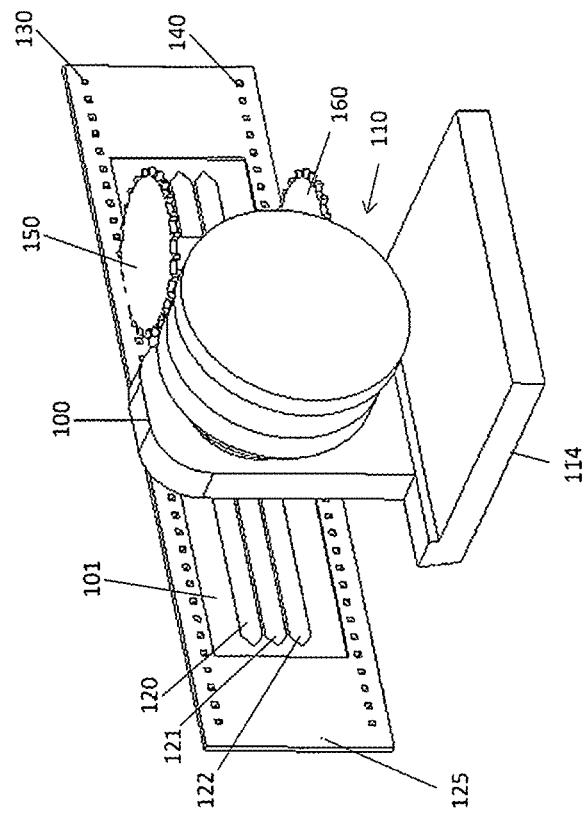
FIG. 3A and FIG. 3B show front and rear perspective views of a film sprocket mechanism for translating a flow cell relative to a detection apparatus.
Figure 3A:
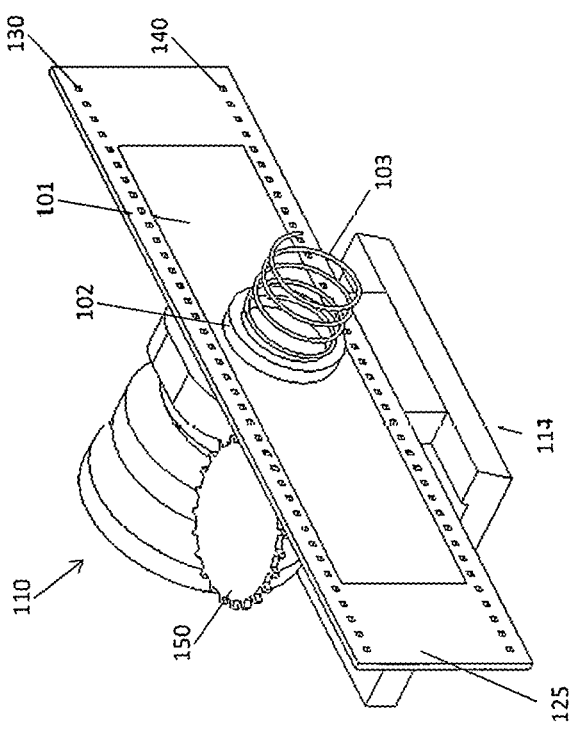

In some embodiments, the scan actuator can use a film sprocket mechanism. The vessel that is to be translated, or a cartridge that holds the vessel, can contain a track of perforations that engages a sprocket in a detection apparatus to achieve translation. As shown in the exemplary configuration of FIG. 3, flow cell 101 is housed in cartridge 125, which contains two perforation tracks 130 and 140. Perforation track 130 is located near the top edge of the cartridge 125 and runs parallel to the longest dimension l of the flow cell. Perforation track 140 is located near the opposite edge of the cartridge 125 and also runs parallel to l. Sprockets 150 and 160 are configured to engage perforation tracks 130 and 140, respectively, when urged toward reference surface 117 by the force of preload spring 103. The flow cell 101 can be translated in scan dimension x, which is parallel to l, by rotating the engaged sprockets 150 and 160.

Figure 4C:
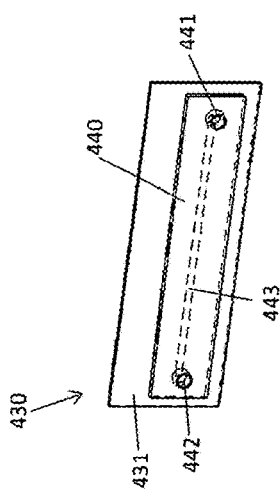
FIG. 4C shows a flow cell.
Figure 4B:
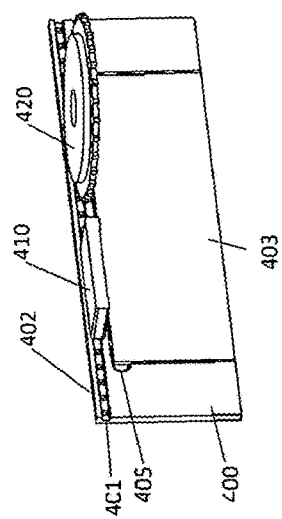
FIG. 4B shows a film sprocket and guide interacting with the flow cell cartridge.
Figure 4A:
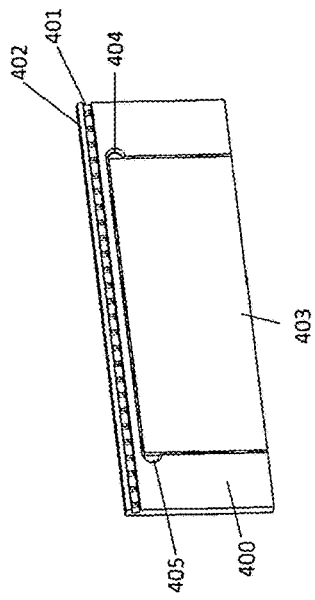
FIG. 4A shows a flow cell cartridge.
Figure 4D:
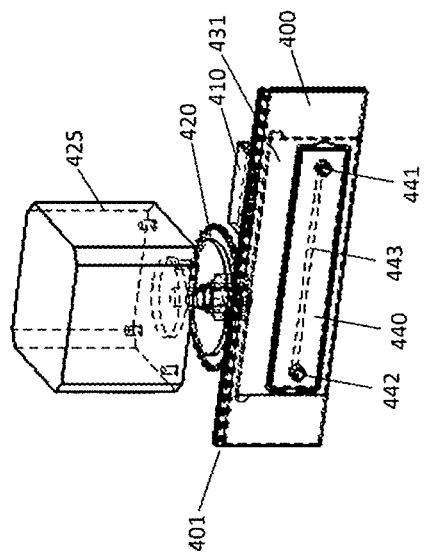
FIG. 4D shows a perspective view of the film sprocket, guide, flow cell cartridge, flow cell and a motor for the film sprocket.

FIG. 4A shows a cartridge 400 having an inset 403 for flow cell 430. The inset includes notches 404 and 405 that are placed to facilitate adjustment or removal of the flow cell 430. Cartridge 400 has a single perforation track 401 near the top edge 402. As shown in FIG. 4B, the perforations are complementary to teeth on sprocket 420 and perforation track 401 is inset into the face of cartridge 400 thereby providing a track that engages guide 410. Guide 410 slots into perforation track 401 to prevent rotation of cartridge 400 in the yaw axis during translation under the action of sprocket 420, thereby preventing unwanted yaw rotation of the flow cell 430 relative to a detector. As shown in FIG. 4C, flow cell 430 includes a bottom plate 431 that is sized for pressure fit with inset 403 and also includes a top plate 440. A channel 443 is formed between plates 431 and 440 due to presence of a spacer or gasket. The top plate 440 also includes holes 441 and 442 which act as inlet and outlet for channel 443. A perspective view of the cartridge 400 with assembled flow cell 430, sprocket 420 with motor 425, and guide 410 is shown in FIG. 4D.

Figure 5B:
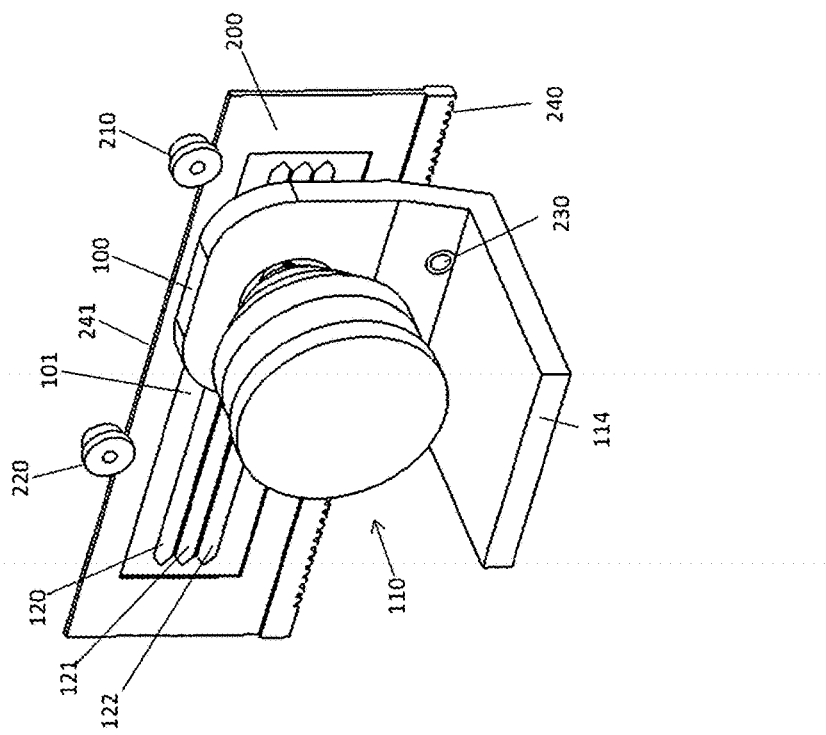
FIG. 5A and FIG. 5B show front and rear perspective views of a spur gear mechanism for translating a flow cell relative to a detection apparatus.
Figure 5A:
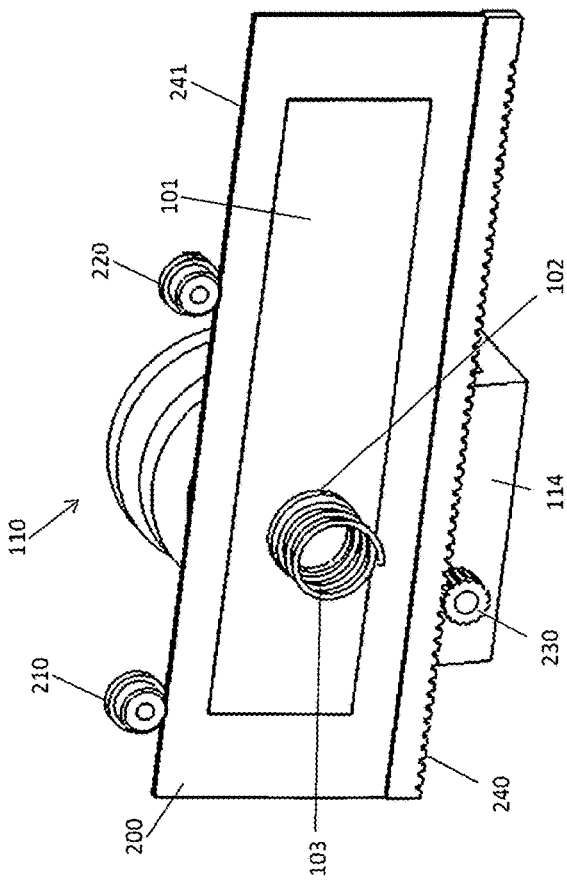

Another useful mechanism for scan actuation is a spur gear that engages teeth on an edge of a flow cell, or on an edge of a cartridge holding the flow cell. FIG. 5A shows cartridge 200 which is pressure fitted to flow cell 101, and which has a serrated bottom edge 240 and smooth top edge 241. Serrated bottom edge 240 engages spur gear 230 when cartridge 200 is urged by preload spring 103 to contact a reference surface on rigid body 100. The cartridge 200 and flow cell 101 are translated by rotating spur gear 230. Wheel guides 210 and 220 engage the smooth edge 241 of the cartridge 200, when the cartridge 200 is positioned to contact the flow cell 101 with a reference surface on rigid body 100. The wheel guides function to prevent rotation of the cartridge 200 and flow cell 101 about the yaw axis.

Scan actuation can also employ a ball screw that engages a threaded catch on a flow cell, or on a cartridge holding the flow cell. FIG. 6A shows cartridge 300 which is pressure fitted to flow cell 101, and which has a threaded catch 311 on the top and two guide catches 312 and 313 on the bottom. Threaded catch 311 engages screw 310 when cartridge 300 is urged by preload spring 103 to contact a reference surface on rigid body 100. The cartridge 300 and flow cell 101 are translated by rotating screw 310 against threads of catch 311. Guide catches 312 and 313 engage rail 320, when the cartridge 300 is positioned to contact the flow cell 101 with reference surface 117. The guide catches 312 and 313 function to prevent rotation of the cartridge 300 and flow cell 101 about the yaw axis.

Scan actuation can use mechanical contact between the motor and vessel (or vessel cartridge) as exemplified above. Alternatively or additionally, interaction between motor and vessel (or vessel cartridge) can be mediated by magnetic attraction. For example, the vessel or cartridge can have a magnetic or ferromagnetic material that interacts with a magnetic or ferromagnetic component of the actuator.

Whether using mechanical contact or other interactions to mediate actuation, a linear motor can be used to drive the scanning motion. Exemplary linear motors that can be used include synchronous linear motors, induction linear motors, homopolar linear motors and piezo electric linear motors.

An apparatus of the present disclosure can further include a y actuator configured to change the relative translational position of the detector and the vessel along the y dimension. Taking as an example the apparatus shown in FIG. 2, a y actuator can operate, for example, by changing the relative translational position of the objective 110 and the reference surface 117. Alternatively or additionally, a y actuator can operate by changing the relative translational position of the flow cell 101 and the reference surface 117. Translation along the y dimension can allow different lanes of a flow cell to be addressed. When a lane is wider than the field of view for the objective, y translation can be used to detect multiple swaths of the lane (i.e. a first swath can be detected by a scan along x and a second swath can be addressed by a step along the y dimension followed by a second scan along x). A y actuator can be configured similarly to the x actuators exemplified herein. For example, a y actuator can be configured to translate the flow cell while it is urged to a reference surface by a preload. Other stepper motors or translation actuators can be used as well for x or y translation.

In particular embodiments, an apparatus of the present disclosure can include a rotational actuator configured to change the relative translational position of the detector and the vessel along an arcuate path. Taking the exemplary flow cell oriented as shown in FIG. 1 a rotational actuator can rotate the flow cell in the yaw axis. Rotation in the yaw axis can be particularly useful for scanning lanes or features that follow an arcuate path. An additional or alternative rotational actuator can rotate a vessel along the roll axis. Rotation in the yaw axis can be particularly useful when the vessel is a tube or cylinder that is oriented to have its length along the x axis.

Several embodiments of the present disclosure are exemplified with regard to an objective having several lenses for gathering and focusing radiation from an object (e.g. a vessel such as a flow cell). It will be understood that any of a variety of optical elements can serve as an objective in an apparatus or method of the present disclosure including, for example, a lens, mirror, fiber optic, fiber bundle, lens array or other optical element that gathers radiation from an object being observed, whether or not the optical element is also capable of focusing the radiation. Objectives or other optical components used in an apparatus or method set forth herein can be configured to transmit radiation in any of a variety of spectral ranges including, but not limited to X-ray, ultraviolet (UV), visible (VIS), infrared (IR), microwave and/or radio wave ranges.

An objective that is used in an apparatus set forth herein can be placed to direct radiation from the internal surface or the lumen of a vessel, through the wall of the vessel and to a detector when the external surface of the vessel contacts a reference surface. In particular embodiments, an objective, and other optional components of an optical system, can be configured for epi-illumination luminescence detection (i.e. epi-luminescence), whereby excitation radiation is directed from a radiation source, through the objective, then through the wall of the vessel to the internal surface or the lumen of the vessel; and whereby emission from the internal surface or the lumen of the vessel is directed back through the wall and through the objective (i.e. excitation and emission both pass through the objective). Alternatively, objectives, and other optional components of an optical system, can be configured for trans-illumination fluorescence, whereby excitation radiation is directed from a radiation source through a first wall of a vessel to the internal surface or the lumen of the vessel; and whereby emission from the internal surface or the lumen of the vessel is directed through another wall of the vessel and through the objective (i.e. emission passes through the objective, excitation does not). Other useful configurations for fluorescence detection include those that excite a vessel via total internal reflection fluorescence (TIRF) or via waveguides. In any of a variety of configurations, the radiation source can form a structural loop with a reference surface such that a vessel that contacts the reference under the urging of a preload will be properly oriented with respect to the radiation source.

The objectives shown in FIGS. 2, 3, 5 and 6 are exemplary, having 4 lenses. Any number or type of lenses can be included to suit a particular application. Particularly useful objectives will have a numerical aperture that is at least 0.1 and at most 0.9. Numerical apertures above 0.95 can be achieved using an immersion objective as set forth in further detail below. An objective or other transmitter can be configured to operate with a detection system that resolves features (e.g. nucleic acid sites) on a surface that are separated by less than 100 µm, 50 µm, 10 µm, 5 µm, 1 µm, or 0.5 µm. The detection system, including objective or other transmitter, can be configured to resolve features having an area on a surface that is smaller than about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$.

An optical system used in an apparatus or method set forth herein can have a field of view that is at least 0.1 mm$^2$, 0.5 mm$^2$, 1 mm$^2$, 2 mm$^2$, 3 mm$^2$, 4 mm$^2$ or higher. Alternatively and/or additionally, the field of view can be configured to be at most 4 mm$^2$, 3 mm$^2$, 2 mm$^2$, 1 mm$^2$, 0.5 mm$^2$, 0.1 mm$^2$, or less.

The objective, or other appropriate component of a detection system used in an apparatus set forth herein, can be configured to focus on analytes that are in or on the vessel. For example, the apparatus can include a focus actuator configured to change the relative position of the objective and the reference surface in the focus dimension z. Physically aligning the vessel to the reference surface under force of a preload effectively fixes the position of the vessel in the z dimension, thereby favoring accurate and robust focusing throughout a scanning operation.

An apparatus set forth herein can employ optical subsystems or components used in nucleic acid sequencing systems. Several such detection apparatus are configured for optical detection, for example, detection of fluorescent signals. Examples of detection apparatus and components thereof that can be used to detect a vessel herein are described, for example, in US Pat. App. Pub. No. 2010/0111768 A1 or U.S. Pat. Nos. 7,329,860; 8,951,781 or 9,193,996, each of which is incorporated herein by reference. Other detection apparatus include those commercialized for nucleic acid sequencing such as those provided by Illumina™, Inc. (e.g. HiSeg™, MiSeg™, NextSeg™, or NovaSeg™ systems), Life Technologies™ (e.g. ABI PRISM™, or SOLiD™ systems), Pacific Biosciences (e.g. systems using SMRT™ Technology such as the Sequel™ or RS II™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety. In particular embodiments, the stage of a known sequencing system can be replaced with a scanning apparatus set forth herein.

Generally, an objective is the optical element of the detection apparatus that is proximal (i.e. closest to) the vessel that is to be detected (e.g. flow cell). In some embodiments, the vessel need not include any optical components. In alternative embodiments, one or more optical component, such as a lens or fiber optic, can be provided by a vessel or by a cartridge to which the vessel is attached. For example, the objective of the detection apparatus can be configured to direct excitation, emission or other signals to the optical component that is present on the vessel or cartridge. Thus, the optical component that is proximal to the sample can be provided by the detection apparatus, or alternatively, by the vessel that houses the sample.

A detection apparatus that is used to observe a vessel in a method or apparatus set forth herein need not be capable of optical detection. For example, the detector can be an electronic detector used for detection of protons or pyrophosphate (see, for example, US Pat. App. Pub. Nos. 2009/0026082 A1; 2009/0127589 A1; 2010/0137143 A1; or 2010/0282617 A1, each of which is incorporated herein by reference in its entirety, or the Ion Torrent™ systems commercially available from ThermoFisher, Waltham, Mass.) or as used in detection of nanopores such as those commercialized by Oxford Nanopore™, Oxford UK (e.g. MinION™ or PromethION™ systems) or set forth in U.S. Pat. No. 7,001,792; Soni & Meller, Clin. Chem. 53, 1996-2001 (2007); Healy, Nanomed. 2, 459-481 (2007); or Cockroft, et al. J. Am. Chem. Soc. 130, 818-820 (2008), each of which is incorporated herein by reference.

In a particular embodiments, apparatus or methods set forth herein can be configured for scanning electron microscopy (SEM). Accordingly, an electron beam can be produced by an electron gun and directed to a vessel by one or more condenser lenses, scanning coils and/or deflector plates. Signal can be detected using an electron detector such as a scintillator-photomultiplier system (e.g. an Everhart-Thornley detector).

Figure 7B:
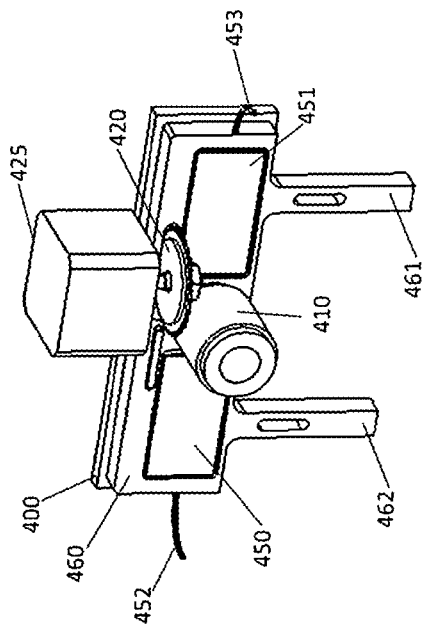
FIG. 7A shows a perspective view of a heating plate and film sprocket scanning mechanism and FIG. 7B shows a perspective view of an objective and the heating plate and film sprocket scanning mechanism.
Figure 7A:
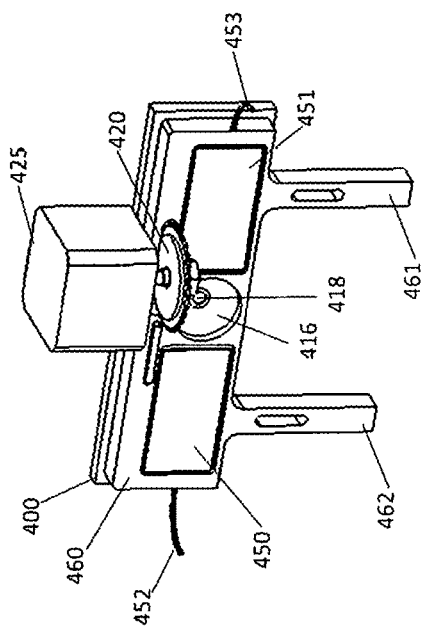

In particular embodiments, a detection apparatus or other apparatus of the present disclosure can provide temperature control of a vessel that is to be detected. Temperature control can be provided by controlling temperature of an internal chamber that houses the vessel. Alternatively or additionally, a vessel that is to be detected can be placed into contact with a thermally conductive surface that is temperature controlled. FIG. 7A shows an exemplary configuration for achieving temperature control of a flow cell via contact with a thermally conductive surface. The backside of aluminum body 460 is attached to two thermal elements 450 and 451 which are located left and right of conical depression 416. The thermal elements can be polyimide thermofoil heaters, Peltier elements, metal heating elements, ceramic heating elements, polymer PTC heating elements or the like. Aluminum body 460 also includes two legs 461 and 462 for attachment to the detection apparatus. As such the two legs form part of the structural loop between the reference surface on the aluminum body 460 and the detection apparatus. Optionally, legs 461 and 462 can be made from a material having low thermal conductivity. Thus, the legs can function to attach the aluminum body to a detection apparatus in a way that insulates other components of the detection apparatus from experiencing unwanted temperature fluctuations. Thermal elements 450 and 451 can be activated via wires 452 and 453 to heat or cool aluminum body 460 such that a flow cell in cartridge 400 is in contact with the opposite side of aluminum body 460 and thus is temperature controlled. As shown in FIG. 7B, conical depression 416 is configured to accept an objective 410 for detection of a flow cell in cartridge 400 through window 418. In the configuration shown, the flow cell cartridge 400 is translated via film sprocket 420 under the control of rotary motor 425.

A detection apparatus or other apparatus of the present disclosure can include a fluidics system for delivering reagents to a vessel that is to be detected. Accordingly, one or more reservoirs can be fluidically connected to an inlet valve of the vessel. The apparatus can further include a pressure supply for driving reagents from reservoirs to the vessel. The apparatus can include a waste reservoir that is fluidically connected to the vessel to remove spent reagents. Taking as an example an embodiment where the vessel is a flow cell, reagents can be delivered via pump to the flow cell through the inlet and then the reagents can flow through the flow cell outlet to a waste reservoir. The reservoirs can include reagents for any of a variety of analytical procedures including, but not limited to nucleic acid sequencing, nucleic acid genotyping, nucleic acid expression analysis, protein sequencing, protein binding analysis (e.g. ELISA), small molecule receptor binding, protein phosphorylation analysis, nucleic acid synthesis or protein synthesis. Alternatively or additionally, the reservoirs can include reagents for a preparative process. Exemplary preparative processes include, but are not limited to, nucleic acid synthesis, peptide synthesis, assembly of oligonucleotides into genes, photolithography, nanofabrication or microfabrication (e.g. via laser etching), laser ablation, or the like.

A fluidic system can include at least one manifold and/or at least one valve for directing reagents from reservoirs to a vessel where detection occurs. Manifolds are particularly useful in sequencing instruments due to the relatively large number of different reagents that are delivered during a sequencing protocol. Exemplary protocols and useful reagents are set forth in further detail below and in references that are incorporated herein by reference. Fluid flow from the reservoirs can be selected via valves such as a solenoid valve (e.g. those made by Takasago Electric, Japan), ball valve, diaphragm valve or rotary valve.

One or more fluidic components used in a detection apparatus or other apparatus of the present disclosure can be housed in a fluidic caddy that is separable from detection components. An exemplary fluidic caddy 600 is shown in FIG. 8A. Fluidic caddy 600 includes a housing 601 having sufficient internal volume to house reagent reservoirs 603, waste reservoirs 602, and a piston shaft 604 for an external pump. Any of a variety of fluidic components can be housed in a fluidic caddy including, but not limited to, one or more reservoirs, fluid lines, valves or pumps. The fluidic caddy includes latches 610 and 611 which are configured to engage with hooks in a detection apparatus. See for example, switch hook 701 in FIG. 9. Flow cell 430 is held within cartridge 400 and cartridge 400 is held to the fluidic caddy 600 via hook 616 and guides 616 and 617. As shown in the expanded cutout of FIG. 8B and in side-view FIG. 8D, hook 615 includes a tooth 614 that inserts into track 401 to hold the cartridge 400 in place. Guides 616 and 617 complete a three-point attachment by engaging the bottom edge of cartridge 400. Preload 620, although shown in retracted position in FIG. 8D, can be extended to push against the back side of the cartridge 400, thereby functioning with hook 615 and guides 616 and 617 to hold the cartridge in place by compressive forces.

Figure 8F:
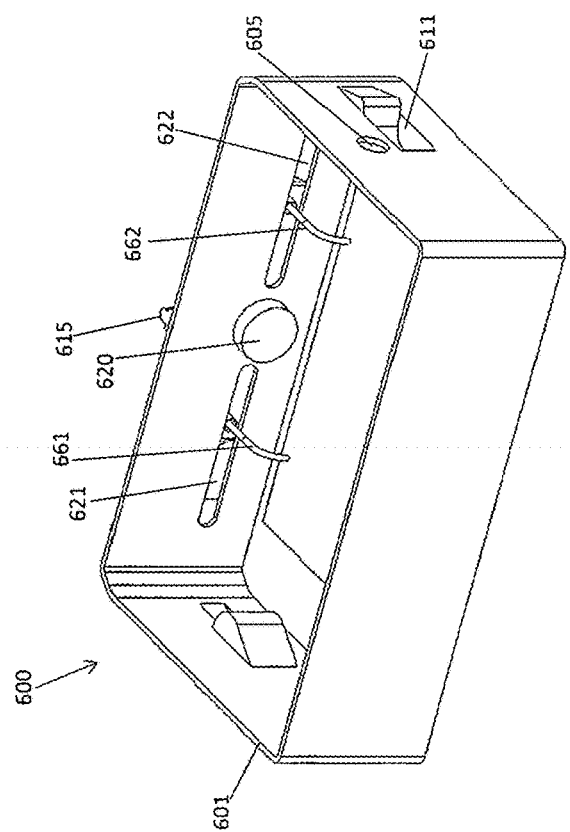
FIG. 8F shows a perspective view of the fluidic caddy emptied of several fluidic components.
Figure 8E:
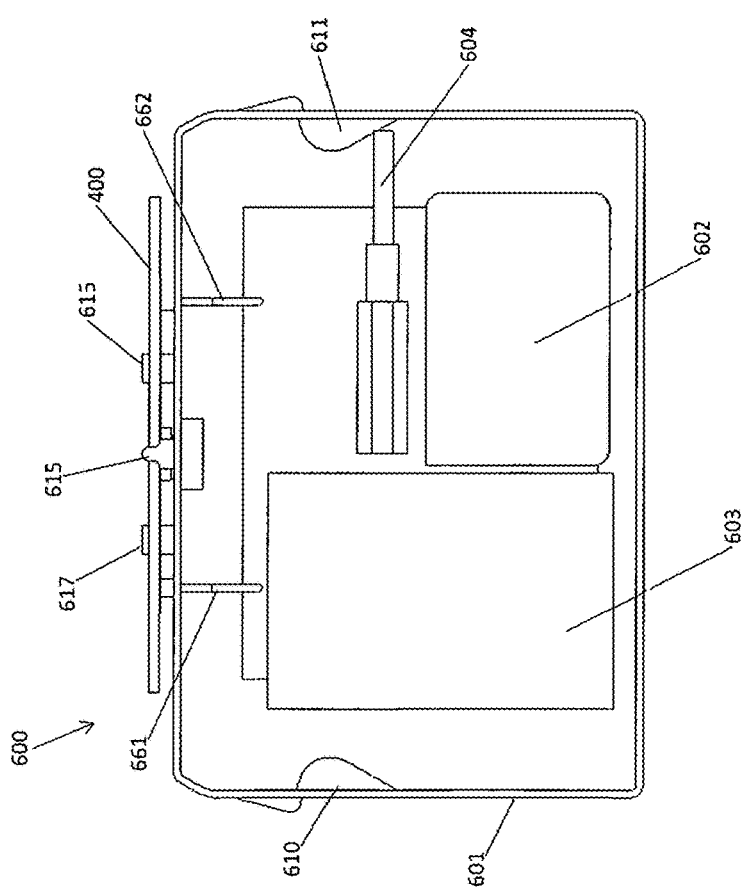
FIG. 8E shows a top view of the fluidic caddy with attached flow cell.

Fluidic caddy 600 includes openings as shown in FIG. 8D and FIG. 8F. For purposes of showing fluidic connections for the flow cell 430, FIG. 8F shows a perspective view of caddy 600 that has been emptied of several other fluidic components. Opening 605 is configured to accept the piston of an external pump. The piston can be driven by a detection apparatus to allow control of fluid flow through flow cell 430 during an analytical procedure (e.g. a nucleic acid sequencing procedure), but the piston need not directly contact any fluids in the caddy 600 or in the flow cell 430. Accordingly, the detection apparatus can constitute a "dry" component that does not make direct contact with fluids, whereas the caddy 600 and flow cell 430 constitute "wet" components. Fluidic caddy 600 includes two elongated openings 621 and 622 which are configured to accommodate tubes 661 and 662, respectively. The elongated shape allows the tubes to move along the x dimension as the flow cell is translated during scanning. Thus, the tubes can remain engaged with the flow cell and fluidic reservoirs during a scanning operation.

The flow cell 430 can be translated independently of caddy 600 via movement of the cartridge as set forth previously herein, for example, in connection with FIG. 4. As such, caddy 600 remains stationary while flow cell 430 is moved. Alternatively, a flow cell can be attached to a caddy such that the caddy and flow cell are translated as a unit. In a further alternative, one or more detection components of a detection apparatus can be moved while the flow cell and/or fluidic caddy is stationary.

Figure 9B:
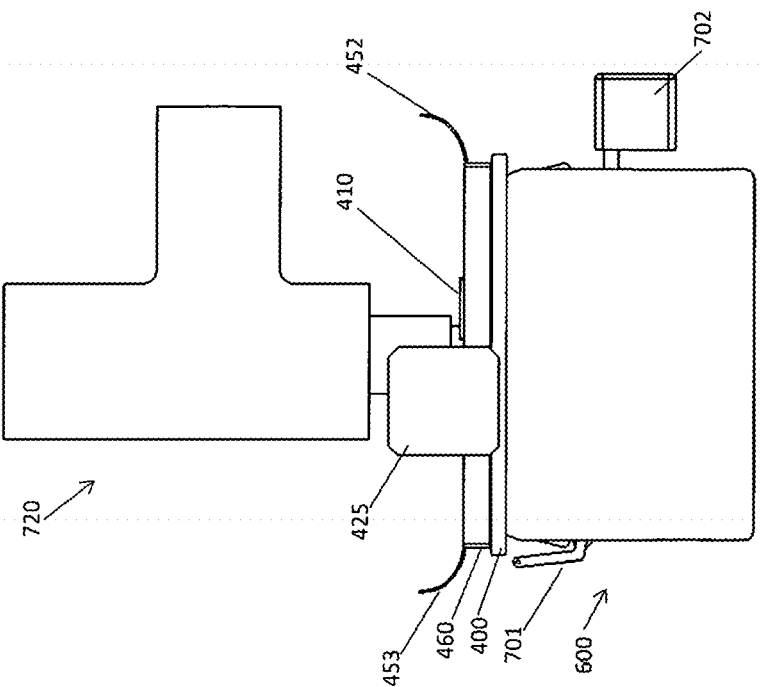
FIG. 9B shows a top view of the fluidic caddy and flow cell interacting with the detection apparatus.
Figure 9A:
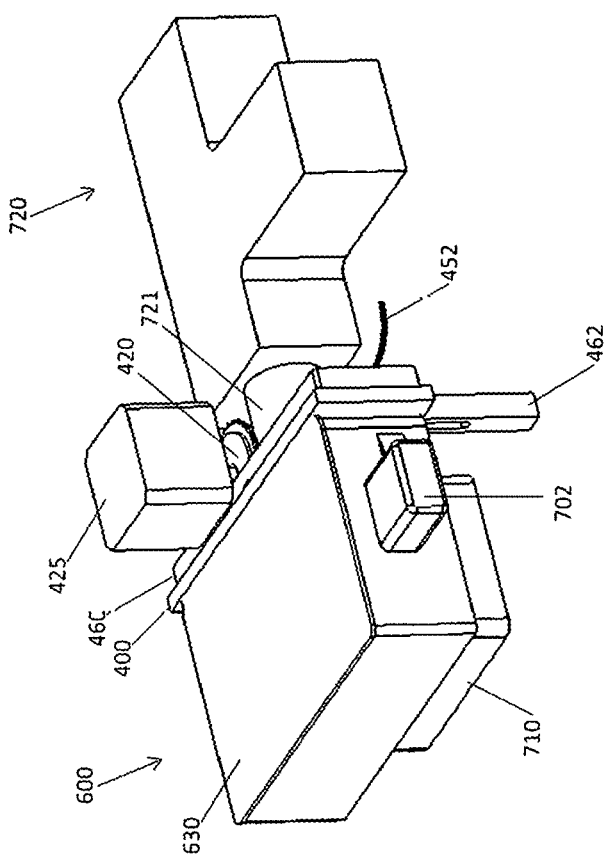
FIG. 9A shows a perspective view of a fluidic caddy and flow cell interacting with a detection apparatus.

Interactions between fluidic caddy 600 and components of a detection apparatus are shown in FIG. 9. The perspective view in FIG. 9A and top view in FIG. 9B, show caddy 600 engaged in a way that sandwiches flow cell cartridge 400 between the caddy 600 and aluminum body 460. When engaged, the flow cell cartridge 400 contacts film sprocket 420 such that motor 425 can drive translation of the flow cell therein. Translation will cause the flow cell to move past objective 721 which is in turn configured to direct fluorescence excitation from fluorometer 720 to the flow cell and to direct fluorescence emission from the flow cell to fluorometer 720.

The mechanism of engaging caddy 600 and flow cell cartridge 400 with a detection apparatus or other apparatus of the present disclosure can be akin to inserting an 8-track cassette into an audio player. The flow cell 430 and cartridge 400 are connected to caddy 600 such that a user need not directly handle the flow cell 430, instead delivering it to the detection apparatus by handling the caddy 600, much like a user need not handle the tape inside of the 8-track cassette. Similarly, individual fluidic components need not be individually handled but can properly engage with actuators in the detection apparatus when the caddy 600 is properly placed in the detection apparatus.

Figure 9C:
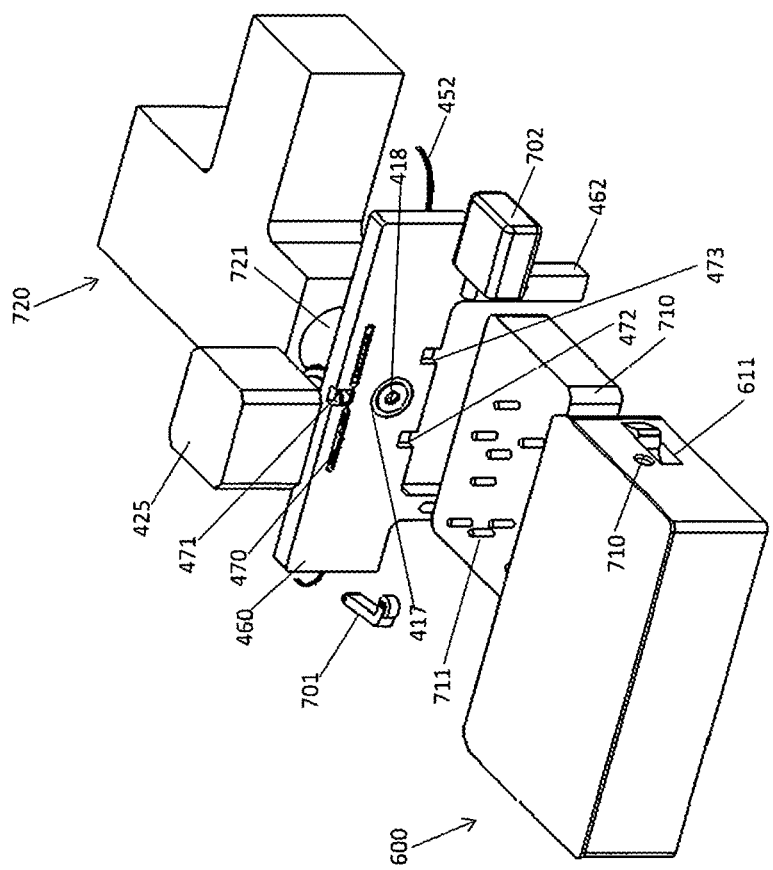
FIG. 9C shows a perspective view of the fluidic caddy disengaged from the detection apparatus.

Fluidic caddy 600 is disengaged from the detection apparatus in FIG. 9C, which illustrates mechanical elements that can be used by the detection apparatus to control function of the fluidic caddy 600. The detection apparatus can include a sensor or switch that responds to presence of the fluidic caddy and actuates functional interactions. In the example of FIG. 9, switch hook 701 is displaced when caddy 600 is properly engaged. This displacement can activate one or more functions. For example, the underside of fluidic caddy 600 can include one or more openings that are positioned to accept one or more valve actuator 711 on platform 710. Valve actuators, although shown in the proud position for purposes of illustration, can be retracted into platform 710 when fluidic caddy 600 is not present. The valve actuators can be raised in response to displacement of switch hook 701 and/or in response to control software for the detection apparatus. Accordingly, the one or more valve actuator 711 can be used to control flow of fluids to the flow cell, from the flow cell, and/or between reservoirs within the caddy. In another example, pump component 702 of the detection apparatus can engage with fluidic components of the caddy 600 via opening 710, for example, by inserting a piston. Interaction of pump component 702 with the fluidic caddy 600 can be actuated directly due to displacement of switch hook 701 and/or in response to control software for the detection apparatus.

The structural loop between the flow cell 430 and fluorometer 720 includes reference surface 417, aluminum body 460, legs 461 and 462, a plate or base to which legs 461 and 462 are attached, and fluorometer 720 which is also attached to the plate or base.

FIG. 10 shows a mechanism that can be used for engaging a flow cell with a detection apparatus. FIG. 10A shows a side view and expanded detail of fluidic cartridge 600 and flow cell cartridge 400 when not engaged with a detection apparatus. When the fluidic caddy 600 is not engaged, flow cell cartridge 400 is in contact with hook 615 and guides 616 and 617. FIG. 10B shows an expanded detail of the configuration that results when caddy 600 is engaged with the detection apparatus. Specifically, flow cell cartridge 400 is moved toward the wall of caddy 600, disengaging from hook 615 and from guides 616 and 617.

Figure 10E:
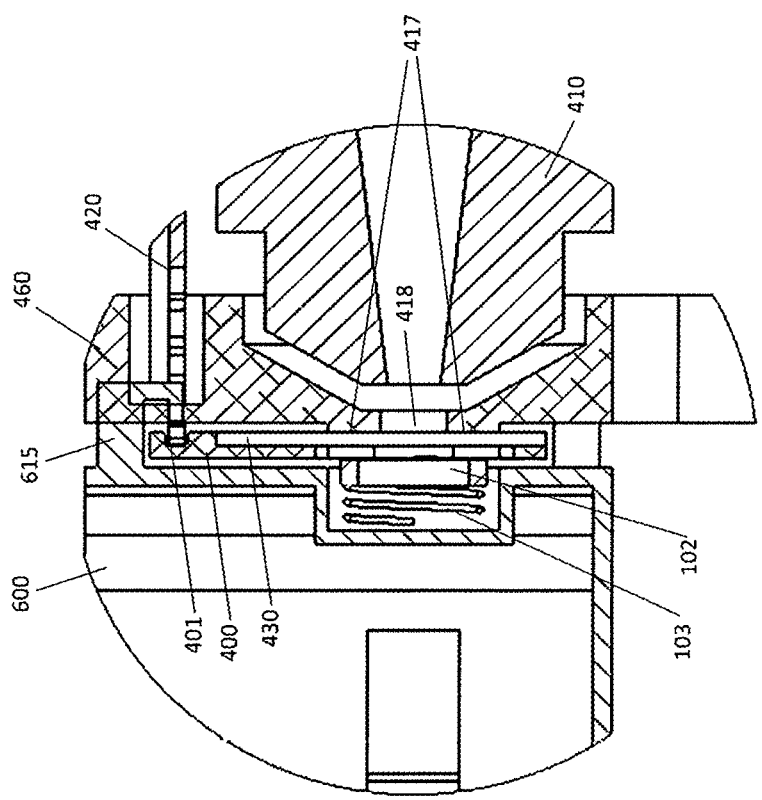
FIG. 10E shows an expanded view of the fluidic caddy engaged with components of a detection apparatus.

A mechanism for changing the position of the flow cell cartridge 400 is shown in FIG. 10E, which is a detail view of the interface between caddy 600, flow cell cartridge 400 and aluminum body 460. FIG. 10E is a detail of FIG. 10D which is a cutaway along line m in FIG. 10C. When the caddy 600 is properly engaged with the detection apparatus, hook 615 and guides 616 and 617 are inserted into notches 471, 472 and 473 in aluminum body 460. The notches 471, 472 and 473 have a sufficient depth that compression of the caddy toward the aluminum body 460 causes the front side of flow cell cartridge 400 to engage sprocket 420 and the front side of flow cell 430 to contact reference surface 417. The compression also results in the back side of flow cell cartridge 400 contacting compression foot 102. In this way, the flow cell 430 is pressed against the reference surface 417 for alignment with objective 410, which observes the flow cell 430 through window 418. The flow cell 430 can be translated via interaction of sprocket 420 with perforation track 401.

Although interactions between a fluidic caddy and detection apparatus have been exemplified herein using mechanical contacts, it will be understood that other mechanical switching mechanisms can be used. Electronic switches can also be used, including for example, those that are activated by electronic sensors (e.g. Bluetooth), magnetic sensors, radio frequency sensors (e.g. RFID), pressure sensors, optical sensors (e.g. barcodes) or the like.

The fluidic caddy and components set forth above are exemplary. Other fluidic caddies and fluidic components that can be used with a detection apparatus of the present disclosure are set forth in commonly owned U.S. patent application Ser. No. 15/922,661, which claims the benefit of U.S. Provisional App. No. 62/481,289, and US Pat. App. Pub. No. 2017/0191125 A1, each of which is incorporated herein by reference. Moreover, a similar fluidic caddy can be used with other apparatus of the present disclosure, such as reactor apparatus, and the other apparatus can be configured as set forth above to interface with a caddy.

Optionally, a detection apparatus or other apparatus of the present disclosure can further include a computer processing unit (CPU) that is configured to operate one or more of the system components set forth herein. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected.

A useful CPU can include, for example, one or more of a personal computer system, server computer system, thin client, thick client, hand-held or laptop device, multiprocessor system, microprocessor-based system, set top box, programmable consumer electronic, network PC, minicomputer system, mainframe computer system, smart phone, or distributed cloud computing environment that includes any of the above systems or devices. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to control one or more component of an apparatus set forth herein or to carry out one or more portions of a method set forth herein. For example, executable instructions may include an operating system, one or more application programs, other program modules, and program data. Generally, program modules may include routines, programs, objects, components, logic, data structures, and so on, that perform particular tasks such as processing of signals detected in a method set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a user with the nucleic acid detection system. Similarly, the CPU can communicate with other devices (e.g., via network card, modem, etc.). Such communication can occur via I/O interfaces. Furthermore, a CPU of a system herein may communicate with one or more networks such as a local area network (LAN), a general wide area network (WAN), and/or a public network (e.g., the Internet) via a suitable network adapter.

FIG. 11 shows a cutaway profile view of an exemplary optical arrangement that uses immersion optics. The arrangement includes an objective 710 that includes a housing 720 and several lenses 711, 712 and 715. The number, position and shape of the lenses is exemplary and can vary according to desired prescription. Also included is rigid body 700, flow cell 701 and flow cell cartridge 702. Flow cell cartridge 702 includes inlet 741 and outlet 742 for moving fluid reagents into and out of the flow cell. The bottom side of rigid body 700 has a reference surface 717 that becomes sealed by flow cell 710 when a preload is applied, for example, as set forth using configurations set forth above. Opposite this seal, rigid body 700 includes a conical depression 716 that is shaped to accept the tip of objective 710. The space 716 between rigid body 700, objective 710 and the seal can be filled with an immersion fluid, such as an oil or aqueous solvent that is index matched to the objective. As such, the immersion fluid will directly contact the proximal lens 715 of objective 710 and the surface of flow cell 701. The fluid can be maintained in the space 716 by seals 731 and 732, which are optionally flexible. Fluid can be added and/or removed from space 716 via line 733. Immersion optics can provide several advantages over optics that image through air including, for example, the ability to achieve numerical aperture (NA) greater than 0.95, ability to image at greater depths into a vessel, and alleviating tolerances on the thickness and uniformity of vessel walls through which the objective resolves objects.

The present disclosure provides methods that are particularly useful for performing cyclical reactions. Each cycle can include delivering reagents for the reaction to a flow cell or other vessel where, optionally, the reaction, or products of the reaction, will be observed. Each cycle can further include scanning of the vessel using apparatus or methods set forth herein. The methods are exemplified herein in the context of a nucleic acid sequencing reaction. However, those skilled in the art will understand from the teaching herein how to modify the methods, and the apparatus, for other cyclical reactions such as nucleic acid synthesis reactions, peptide sequencing reactions, peptide synthesis reactions, combinatorial small molecule synthesis reactions or the like. However, the method need not be cyclical and can instead be carried out in a non-repetitive configuration, for example, to observe a single reaction or phenomenon.

Particularly useful sequencing reactions are Sequencing By Binding™ (SBB™) reactions as described in commonly owned US Pat. App. Pub. No. 2017/0022553 A1; U.S. Pat. App. Ser. No. 62/447,319 to which US Pat App. Pub. No. 2018/0044727 A1 claims priority; 62/440,624 to which US Pat App. Pub. No. 2018/0187245 A1 claims priority; or 62/450,397 to which US Pat App. Pub. No. 2018/0208983 A1 claims priority, each of which is incorporated herein by reference. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

The examination phase can be carried out in a flow cell (or other vessel), the flow cell containing at least one template nucleic acid molecule primed with a primer by delivering to the flow cell reagents to form a first reaction mixture. The reaction mixture can include the primed template nucleic acid, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell. Detection can be carried out by scanning the flow cell using an apparatus or method set forth herein.

During the examination phase, discrimination between correct and incorrect nucleotides can be facilitated by ternary complex stabilization. A variety of conditions and reagents can be useful. For example, the primer can contain a reversible blocking moiety that prevents covalent attachment of nucleotide; and/or cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety. The examination phase can include scanning of the flow cell using apparatus and methods set forth herein.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

It will be understood that any of a variety of nucleic acid sequencing reactions can be carried out using an apparatus and method of the present disclosure. Other exemplary sequencing methods are set forth below.

Sequencing-by-synthesis (SBS) techniques can be used. SBS generally involves the enzymatic extension of a nascent primer through the iterative addition of nucleotides against a template strand to which the primer is hybridized. Briefly, SBS can be initiated by contacting target nucleic acids, attached to sites in a vessel, with one or more labeled nucleotides, DNA polymerase, etc. Those sites where a primer is extended using the target nucleic acid as template will incorporate a labeled nucleotide that can be detected. Detection can include scanning using an apparatus or method set forth herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the vessel (before or after detection occurs). Washes can be carried out between the various delivery steps. The cycle can be performed n times to extend the primer by n nucleotides, thereby detecting a sequence of length n. Exemplary SBS procedures, reagents and detection components that can be readily adapted for use with a detection apparatus produced by the methods of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.).

Some SBS embodiments include detection of a proton released upon incorporation of a nucleotide into an extension product. For example, sequencing based on detection of released protons can use reagents and an electrical detector that are commercially available from ThermoFisher (Waltham, Mass.) or described in US Pat. App. Pub. Nos. 2009/0026082 A1; 2009/0127589 A1; 2010/0137143 A1; or 2010/0282617 A1, each of which is incorporated herein by reference.

Other sequencing procedures can be used, such as pyrosequencing. Pyrosequencing detects the release of inorganic pyrophosphate (PPi) as nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference).

In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system that is configured to scan a vessel using apparatus and methods set forth herein.

Sequencing-by-ligation reactions are also useful including, for example, those described in Shendure et al. *Science* 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template, for example, using a scanning apparatus or method set forth herein.

Some embodiments can utilize methods involving real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zero-mode waveguides (ZMW). Techniques and reagents for sequencing via FRET and or ZMW detection that can be modified for use in an apparatus or method set forth herein are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008); or U.S. Pat. Nos. 7,315,019; 8,252,911 or 8,530,164, the disclosures of which are incorporated herein by reference.

Steps for the above sequencing methods can be carried out cyclically. For example, examination and extension steps of an SBB™ method can be repeated such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles of a sequencing method set forth herein can be carried out including, for example, at least 1, 2, 5, 10, 20, 25, 30, 40, 50, 75, 100, 150 or more cycles. Alternatively or additionally, no more than 150, 100, 75, 50, 40, 30, 25, 20, 10, 5, 2 or 1 cycles are carried out.

Nucleic acid template(s), to be sequenced, can be added to a vessel using any of a variety of known methods. In some embodiments, a single nucleic acid molecule is to be sequenced. The nucleic acid molecule can be delivered to a vessel and can optionally be attached to a surface in the vessel. In some embodiments, the molecule is subjected to single molecule sequencing. Alternatively, multiple copies of the nucleic acid can be made and the resulting ensemble can be sequenced. For example, the nucleic acid can be amplified on a surface (e.g. on the inner wall of a flow cell) using techniques set forth in further detail below.

In multiplex embodiments, a variety of different nucleic acid molecules (i.e. a population having a variety of different sequences) are sequenced. The molecules can optionally be attached to a surface in a vessel. The nucleic acids can be attached at unique sites on the surface and single nucleic acid molecules that are spatially distinguishable one from the other can be sequenced in parallel. Alternatively, the nucleic acids can be amplified on the surface to produce a plurality of surface attached ensembles. The ensembles can be spatially distinguishable and sequenced in parallel.

A method set forth herein can use any of a variety of amplification techniques in a vessel. Exemplary techniques that can be used include, but are not limited to, polymerase chain reaction (PCR), rolling circle amplification (RCA), multiple displacement amplification (MDA), bridge amplification, or random prime amplification (RPA). In particular embodiments, one or more primers used for amplification can be attached to a surface in a vessel. In such embodiments, extension of the surface-attached primers along template nucleic acids will result in copies of the templates being attached to the surface. Methods that result in one or more sites on a solid support, where each site is attached to multiple copies of a particular nucleic acid template, can be referred to as "clustering" methods.

In PCR embodiments, one or both primers used for amplification can be attached to a surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. Nos. 5,641,658 or 7,115,400; U.S. Patent Pub. Nos. 2002/0055100 A 1, 2004/0096853 A 1, 2004/0002090 A1, 2007/0128624 A1 or 2008/0009420 A1, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a vessel.

In particular embodiments, a combination of the above-exemplified amplification techniques can be used. For example, RCA and MDA can be used in a combination wherein RCA is used to generate a concatemeric amplicon in solution (e.g. using solution-phase primers). The amplicon can then be used as a template for MDA using primers that are attached to a surface in a vessel. In this example, amplicons produced after the combined RCA and MDA steps will be attached in the vessel. The amplicons will generally contain concatemeric repeats of a target nucleotide sequence.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *pneumocystis carinii, Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli*, staphylococci or *mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference. Cells, tissues, biological fluids, proteins and other samples can be obtained from these organisms and detected using an apparatus or method set forth herein.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

The present disclosure further provides a detection apparatus that includes (a) a vessel having a lumen and a wall, wherein the wall has an internal surface and an external surface, wherein the wall has a plurality of discrete contacts between the internal surface and the external surface, wherein the internal surface contacts the lumen, and wherein the plurality of discrete contacts occupies a length l in a scan dimension x; (b) a transmissive surface; (c) a preload configured to urge discrete contacts on the external surface of the vessel to contact the transmissive surface, optionally, the area of the transmissive surface can have a maximum length in the scan dimension x that is shorter than length l; (d) a scan actuator configured to slide the vessel along the transmissive surface in the scan dimension x; and (e) a detector configured to acquire signals from the discrete contacts via the transmissive surface.

As exemplified in several embodiments herein, optical signals can be relayed to a detection apparatus via transmissive surface that is transparent to optical signals. An objective serves as a useful transmitter of optical signals from a vessel to a detector. In some embodiments the transmitter is an array of lenses. The lenses in the array can be configured to collect signals from (or direct energy to) different areas in an xy plane. The lenses can be arranged to collect signals from contiguous areas in the xy plane or, alternatively, the areas that are observed can be separated by interstitial regions that are not observed when the areas are observed. In some embodiments, the vessel includes an array of sites that is configured to be observed by an array of lenses. Each lens can be configured to simultaneously observe one or more sites in the array of sites. For example, each lens can be configured to observe at least 1, 4, 9, 16, 25, 36, 49, 64, 81, 100 or more sites in an array of sites. Alternatively or additionally, each lens can be configured to observe at most 100, 81, 64, 49, 36, 25, 16, 9, 4 or 1 site(s) in an array of sites. Accordingly, an embodiment is provided wherein each lens is configured to observe a single site.

Each lens in an array of lenses can be aligned with its own optical train to direct radiation to one or more detector. Alternatively, multiple lenses can be combined into a common optical train to direct radiation to one or more detector. The optical trains can include any of a variety of optical components including, but not limited to, a collimating lens for collimating signals from the array of sites, a color separating element for spectrally separating radiation; and a focusing lens for focusing radiation from the sites to a detector. Exemplary configurations for an array of lenses and an array of sites observed by the lenses is provides in U.S. Pat. No. 9,581,550, which is incorporated herein by reference. For example, the sites of the array can be zero mode waveguides (ZMWs).

Other transmitters can be used as appropriate for the energy or signal that is to be transmitted. For example, a transmissive surface can conduct electrical signals, thermal signals, magnetic signals, pressure signals, audio signals, or the like. Temporary electrical contacts such as pogo pins can be used to transmit electrical signals between the transmissive surface and vessel. A transmitter that is present in an apparatus set forth herein can transmit energy of a variety of forms, including but not limited to the aforementioned signals.

In a particular embodiment, the transmissive surface or the internal surface of the vessel includes an electronic detector such as a field-effect transistor (FET) or complementary metal oxide semiconductor (CMOS). Particularly useful electronic detectors include, for example, those used for nucleic acid sequencing applications such as those used for detection of protons as set forth in US Pat. App. Pub. Nos. 2009/0026082 A1; 2009/0127589 A1; 2010/0137143 A1; or 2010/0282617 A1, each of which is incorporated herein by reference. Also useful are electronic detectors used to detect optical signals including for example, those set forth in US Pat. App. Pub. Nos. 2009/0197326 A1; 2015/0293021 A1; 2016/0017416 A1; or 2016/0356715 A1, each of which is incorporated herein by reference.

The apparatus and methods of the present disclosure have been exemplified in the context of use for nucleic acid sequencing reactions. The apparatus and methods can be used for other analytical applications as well. Generally, analytical applications that are carried out in scanning microscopes can be applied to apparatus and methods of the present disclosure. For example, the methods or apparatus can be configured to scan microarrays that are used for analyzing enzyme activity, binding of ligands to receptors, binding of complementary nucleic acids to each other, presence of mutations (such as single nucleotide polymorphisms (SNPs)) in nucleic acids, expression level for RNA species. Microarrays that are detected via optical labels, such as fluorophores, are particularly applicable. Larger biological samples such as cells or tissues can be detected using a method or apparatus herein. Again, detection modalities that utilize optically detected probes or stains are particularly applicable. Other uses include evaluation of manufactured products for which quality or other characteristics are evaluated via microscopic scanning. Exemplary products include, but are not limited to, computer chips, sensors, electronic components and other devices that are microfabricated or nanofabricated. Tests known in the art of molecular diagnostics can be modified for use in an apparatus or method set forth herein such as binding assays (e.g. enzyme-linked immunosorbent assay (ELISA)), real time polymerase chain reaction assays and the like.

Apparatus and methods set forth herein in the context of detecting reactions can be readily modified for use in preparative methods. In particular embodiments, the present disclosure provides reactor apparatus. A reactor apparatus can include (a) a vessel having a lumen and a wall, wherein the wall has an internal surface and an external surface, wherein the internal surface contacts the lumen; (b) a reference surface that forms a structural loop with an energy source; (c) a preload configured to urge the external surface of the vessel to contact an area on the reference surface; (d) a scan actuator configured to slide the vessel along the reference surface in a scan dimension; and (e) a transmitter configured to direct energy from the energy source to the internal surface or the lumen when the external surface of the vessel is urged by the preload to contact the reference surface.

Also provided is a method of performing reactions in a vessel. The method can include (a) translating a vessel along a reference surface of a reactor apparatus, wherein the vessel comprises a lumen and a wall, wherein the lumen comprises reactants, wherein the reference surface contacts at least a portion of the vessel during the translating, and wherein the reference surface forms a structural loop with an energy source; and (b) directing energy from the energy source to the reactants at different locations along the vessel, wherein the vessel is urged to the reference surface by a preload during the directing of the energy to the reactants, thereby performing reactions in the vessel.

A method of performing reactions can include (a) delivering energy from a reactor apparatus to a first subset of reactants in a vessel while applying a preload to a first portion of the vessel, wherein the preload positions the first subset of reactants to occupy an xy plane of a reaction zone, wherein the preload is not applied to a second portion of the vessel; (b) translating the vessel to position a second subset of the reactants in the xy plane of the reaction zone; and (c) delivering energy from the reactor apparatus to the second subset of the analytes in the vessel while applying the preload to a second portion of the vessel, wherein the preload positions the second subset of the analytes to occupy the xy plane, wherein the preload is not applied to the first portion of the vessel, thereby performing reactions in the vessel.

Exemplary energy sources that can be used in apparatus herein include, but are not limited to, radiation sources such as a laser, light emitting diode (LED), lamp, microwave source, or x-ray generator; electricity source; ion beam source such as a duoplasmitron; electron emitter such as a hot filament or hollow cathode; electric current source; or voltage source.

Throughout this application various publications, patents and/or patent applications have been referenced. The disclosures of these documents in their entireties are hereby incorporated by reference in this application.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

A number of embodiments have been described. Nevertheless, it will be understood that various modifications may be made. Accordingly, other embodiments are within the scope of the following claims.

What is claimed is:

1. A detection apparatus, comprising:
   (a) a vessel comprising a rack, a lumen and a wall, wherein the wall comprises an internal surface and an external surface;
   (b) a detector;
   (c) a rigid body comprising a reference surface, the rigid body fixing the position of the reference surface relative to the position of the detector;
   (d) a preload that urges the external surface of the vessel to be in direct contact with the reference surface;
   (e) a scan actuator comprising a pinion that engages the rack to slide the vessel along the reference surface in a scan dimension without changing the position of the reference surface relative to the position of the detector; and
   (f) a transmitter that directs, to the detector, a signal from the internal surface or the lumen, when the external surface of the vessel is urged by the preload to contact the reference surface.

2. The apparatus of claim 1, wherein the preload applies a pushing force on the vessel.

3. The apparatus of claim 1, wherein the preload has a contact area with the vessel that is no larger than the area of contact between the reference surface and the vessel.

4. The apparatus of claim 1, wherein the preload comprises a compressible material configured to contact the vessel or at least one ball bearing configured to contact the vessel.

5. The apparatus of claim 1, wherein the scan dimension is in an xy plane of a Cartesian coordinate system.

6. The apparatus of claim 5, further comprising a z actuator configured to change the relative position of the transmitter and the reference surface in the z dimension of the Cartesian coordinate system.

7. The apparatus of claim 5, wherein the scan dimension is linear along the x dimension of the xy plane.

8. The apparatus of claim 7, further comprising a y actuator configured to change the relative translational position of the vessel and the reference surface along the y dimension.

9. The apparatus of claim 7, wherein the external surface has length l in scan dimension x, wherein the area of contact on the reference surface has a maximum length in the scan dimension x that is shorter than length l.

10. The apparatus of claim 5, wherein the scan dimension is an arcuate path in the xy plane.

11. The apparatus of claim 5, wherein the transmitter comprises an array of lenses, wherein each lens in the array is configured to observe a discrete area in the xy plane.

12. The apparatus of claim 11, wherein the vessel comprises an array of sites, and wherein each lens in the array of lenses is configured to observe a single site in the array of sites.

13. The apparatus of claim 12, wherein one or more analytes are attached to one or more sites in the array of sites.

14. The apparatus of claim 13, wherein the array comprises at least 1,000 of the sites per $cm^2$ and wherein the detector is configured to distinguish the sites.

15. The apparatus of claim 1, wherein the rack comprises one or more perforations, and wherein the pinion comprises a gear that interacts with the one or more perforations.

16. The apparatus of claim 1, wherein the signal comprises radiation, and wherein the transmitter comprises an optical objective.

17. The apparatus of claim 16, wherein the rigid body comprises an opening for the optical objective and the reference surface surrounds the opening.

18. The apparatus of claim 17, wherein the preload has a contact area with the vessel that is opposite the reference surface that surrounds the opening.

19. The apparatus of claim 1, further comprising a radiation source, the rigid body fixing the position of the reference surface relative to the position of the radiation source.

20. The apparatus of claim 19, wherein energy from the radiation source is directed through the transmitter to the internal surface or the lumen when the external surface of the vessel is urged by the preload to contact the reference surface.

21. The apparatus of claim 19, wherein the radiation source is configured to direct energy through the transmitter and then to the lumen when the external surface of the vessel is urged by the preload to contact the reference surface.

22. The apparatus of claim 1, wherein the vessel comprises a flow cell having an inlet and outlet in fluid communication with the lumen, and wherein the internal surface of the wall comprises an array of nucleic acid sites.

23. The apparatus of claim 1, wherein the preload comprises a compressible material configured to contact the vessel.

24. The apparatus of claim 1, wherein the transmitter is configured to direct, to the detector, a signal from the internal surface, when the external surface of the vessel is urged by the preload to contact the reference surface.

25. The apparatus of claim 24, wherein a plurality of analytes is attached to the internal surface.

26. The apparatus of claim 25, wherein the analytes comprise nucleic acids.

27. The apparatus of claim 25, wherein the analytes comprise ternary complexes, each of the ternary complexes comprising a polymerase, primed nucleic acid and cognate nucleotide.

28. The apparatus of claim 25, wherein the analytes comprise cells.

29. The apparatus of claim 1, wherein the vessel comprises a cartridge that contains a flow cell and the cartridge comprises the rack.

* * * * *